United States Patent
Frinking et al.

(10) Patent No.: US 10,278,612 B2
(45) Date of Patent: May 7, 2019

(54) REAL-TIME PERFUSION IMAGING AND QUANTIFICATION

(75) Inventors: Peter Frinking, Manno (CH); Laurent Mercier, Manno (CH); Nicolas Rognin, Manno (CH); Marcel Arditi, Manno (CH)

(73) Assignee: Bracco Suisse SA (CH)

(*) Notice: Subject to any disclaimer, the term of this patent is extended or adjusted under 35 U.S.C. 154(b) by 422 days.

(21) Appl. No.: 13/127,389

(22) PCT Filed: Nov. 23, 2009

(86) PCT No.: PCT/EP2009/065668
§ 371 (c)(1),
(2), (4) Date: May 3, 2011

(87) PCT Pub. No.: WO2010/058014
PCT Pub. Date: May 27, 2010

(65) Prior Publication Data
US 2011/0213244 A1    Sep. 1, 2011

(30) Foreign Application Priority Data

Nov. 24, 2008  (EP) .................................... 08169794

(51) Int. Cl.
*A61B 5/055* (2006.01)
*A61B 8/06* (2006.01)
(Continued)

(52) U.S. Cl.
CPC ................ *A61B 5/055* (2013.01); *A61B 8/06* (2013.01); *A61B 8/481* (2013.01);
(Continued)

(58) Field of Classification Search
USPC .................................. 600/431, 407, 437, 458
See application file for complete search history.

(56) References Cited

U.S. PATENT DOCUMENTS 5,743,266 A * 4/1998 Levene et al. ................ 600/458
6,436,049 B1    8/2002 Kamiyama et al.
(Continued)

FOREIGN PATENT DOCUMENTS

CN    101087562 A    12/2007
CN    101160097 A    4/2008
(Continued)

*Primary Examiner* — James M Kish
(74) *Attorney, Agent, or Firm* — John M. Janeway; Janeway Patent Law, PLLC

(57) ABSTRACT

A solution for diagnostic applications is proposed. Particularly, a corresponding diagnostic system includes means (903-906) for providing (A1-A3) a plurality of input signals representative of a body-part being perfused with a contrast agent over time, each input signal being indicative of a response to an interrogating stimulus of a corresponding location of the body-part possibly including the contrast agent, means (909-930) for generating (A4.1-A4.3) a plurality of filtered signals from selected input signals of selected locations, each filtered signal at each instant over time being generated from a corresponding selected input signal according to a portion of the selected input signal including said instant, and means (933-939) for monitoring (A4.4-A4.6) each filtered signal to detect a peak in the response to the interrogation stimulus of the corresponding selected location, the peak being detected in response to the fulfillment of a stability condition by a corresponding portion of the filtered signal.

32 Claims, 17 Drawing Sheets

(51) Int. Cl.
   *A61B 8/08*    (2006.01)
   *G01R 33/563*  (2006.01)
   *A61B 6/00*    (2006.01)

(52) U.S. Cl.
   CPC ........ G01R 33/56366 (2013.01); *A61B 6/504* (2013.01); *A61B 6/507* (2013.01); *G01R 33/563* (2013.01)

(56) References Cited

U.S. PATENT DOCUMENTS

2003/0114759 A1* 6/2003 Skyba et al. .................. 600/458
2005/0033179 A1* 2/2005 Gardner et al. ............... 600/458
2008/0294049 A1* 11/2008 Guracar ........................ 600/458

FOREIGN PATENT DOCUMENTS

| JP | 2008-525074 A | 7/2008 |
| WO | 9853855 A1 | 12/1998 |
| WO | WO2006067201 A2 | 6/2006 |
| WO | 2007059615 A1 | 5/2007 |
| WO | WO2008074889 A1 | 6/2008 |

* cited by examiner

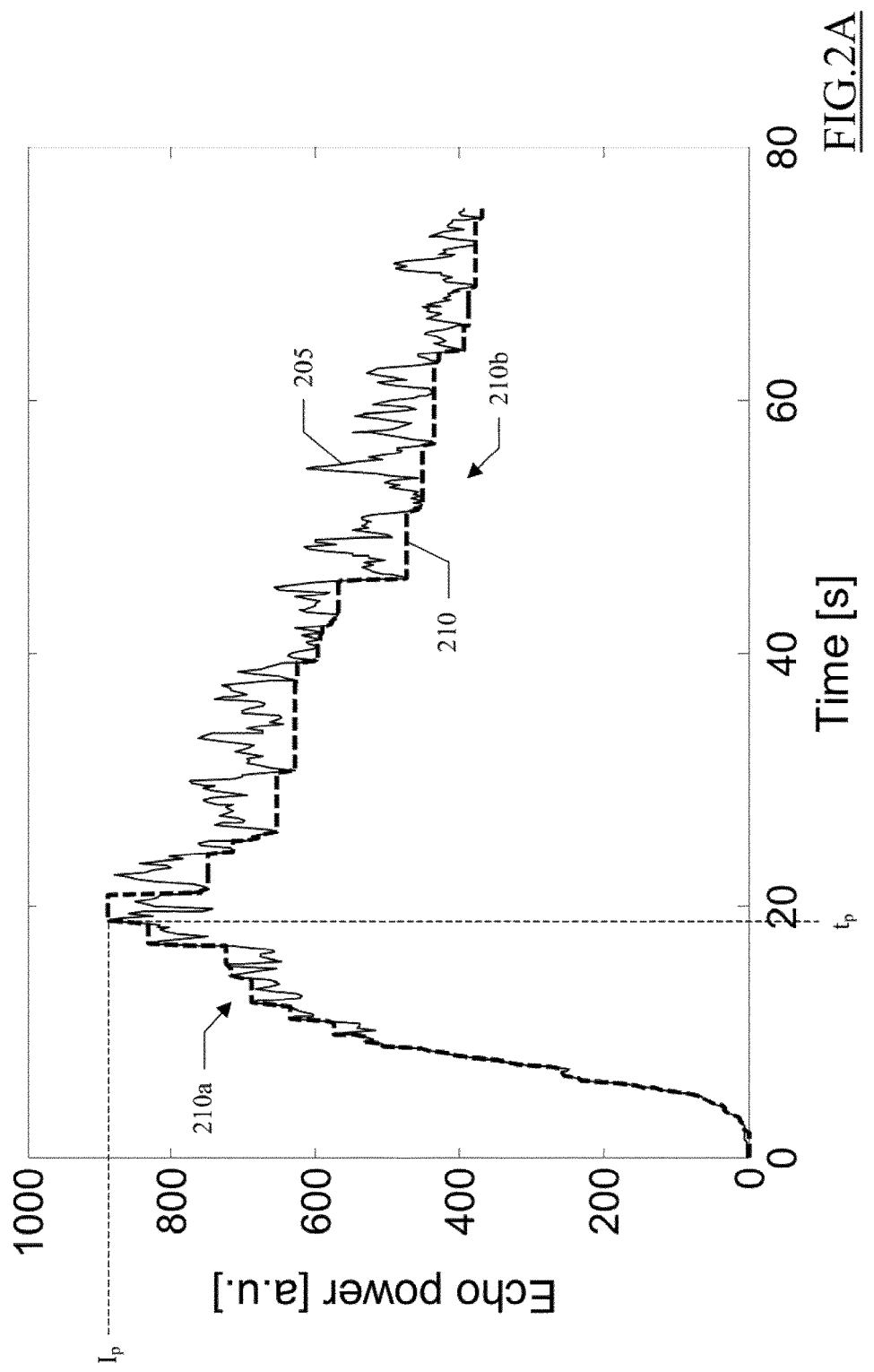

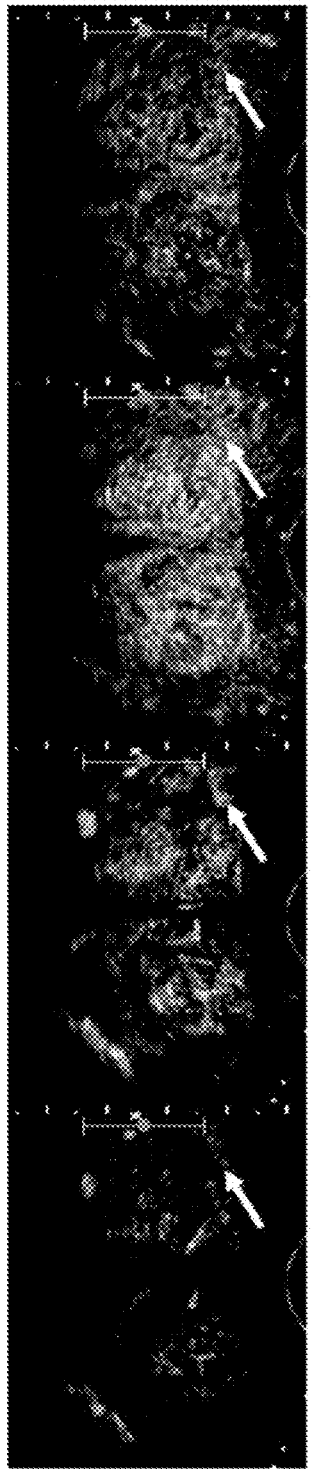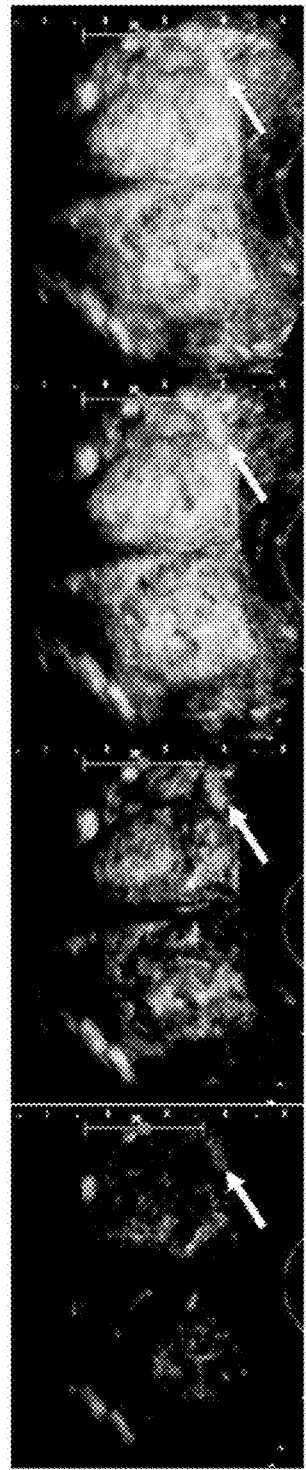
FIG.7A
FIG.7B

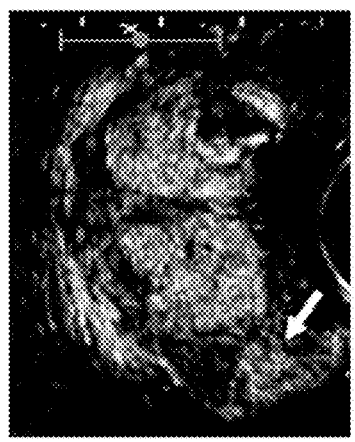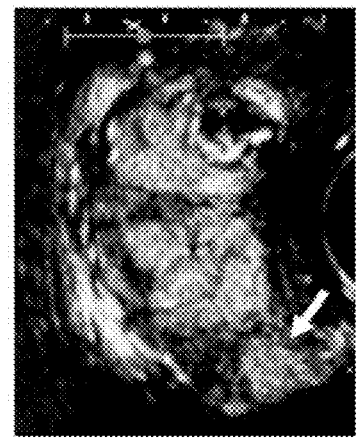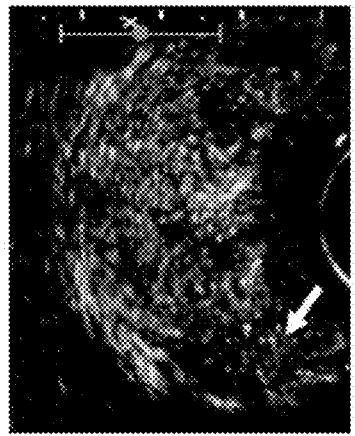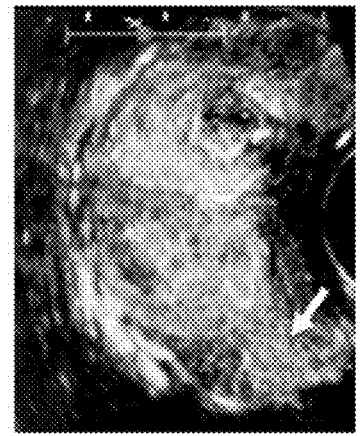
FIG.8A
FIG.8B

REAL-TIME PERFUSION IMAGING AND QUANTIFICATION

TECHNICAL FIELD

The solution according to an embodiment of the present invention relates to the field of medical equipments. More specifically, this solution relates to the field of diagnostic systems.

BACKGROUND OF THE INVENTION

Medical tests are commonly used as tools for the diagnosis of a number of pathologies—e.g., following the report of corresponding symptoms. For this purpose, different techniques are available in the art.

For example, the gold standard technique for cancer diagnosis (e.g., in prostate, liver, and breast) is biopsy, where samples of relevant tissues (commonly referred to as cores) are removed from a patient for examination. However, biopsy is a very invasive and expensive procedure. Moreover, biopsy is relatively inaccurate in specific applications (for example, its success rate is only approximately 70% in prostate cancer diagnosis, even with new strategies based on a higher number of cores).

Contrast-enhanced ultrasound analysis is another diagnostic technique that finds increasing applications in the same field. Generally, this diagnostic technique is based on the administration of an ultrasound contrast agent (UCA) to the patient—for example, a suspension of phospholipid-stabilized gas-filled microvesicles (or microbubbles); these contrast agent microbubbles act as efficient ultrasound reflectors, and can be easily detected by applying ultrasound waves and measuring the echo signals that are returned in response thereto. Since the contrast agent flows at the same velocity as the red-blood cells in the patient, its detection and tracking provides information about blood perfusion in a body-part under analysis (from which information about its condition can be derived).

Particularly, in an imaging approach, image sequences representing an evolution of the contrast agent in the body-part during the perfusion process are generated (where the values of each pixel in the images represent an intensity of the recorded echo signal over time for a corresponding location of the body-part). Therefore, examination of such image sequences (for example, displayed on a monitor) provides only a qualitative indication of the blood perfusion in the body-part.

Conversely, in a quantitative approach, the echo signals recorded during the whole perfusion process are fitted by mathematical model functions (for example, as disclosed in WO-A-2004/110279, the entire disclosure of which is incorporated herein by reference). The instances of the model functions so obtained can then be used to calculate different perfusion parameters (such as a wash-in rate, a wash-out rate, and the like). Any perfusion parameter may be calculated from a global echo signal that is obtained in a pre-defined Region Of Interest (ROI) comprising more than one pixel (with the perfusion parameter that is then presented as a single value). Alternatively, any perfusion parameter may be calculated from the echo signal of each pixel individually; a parametric image is then generated by graphically representing the value of the perfusion parameter for each corresponding pixel (preferably in a color-coded representation). The perfusion parameters provide a quantitative assessment of the blood perfusion in the body-part (with the parametric images representing a spatial map of the perfusion parameters throughout the body-part).

With reference in particular to prostate cancer diagnosis, studies using targeted biopsy under contrast-enhanced ultrasound guidance have shown an increase of its success rate (with the possibility of reducing the number of required cores). Moreover, contrast-enhanced ultrasound analysis could also replace biopsy as the first choice in the prostate cancer diagnosis (with a dramatic reduction of side-effects, costs, and patient morbidity).

For this purpose, the use of contrast-enhanced ultrasound analyses as a tool for the diagnosis of prostate cancer requires detection and characterization of corresponding lesions in the body-part. More specifically, the lesions are detected according to differences in perfusion kinetics compared to normal parenchymal tissue (i.e., earlier and faster wash-in and wash-out of the contrast agent). The lesions can then be characterized (in order to differentiate benign lesions from malignant lesions) according to differences in their vascular properties (i.e., density and/or structure of corresponding microvascular networks).

Parametric analyses may be used to detect the lesions. Indeed, the examination of parametric images based on corresponding perfusion parameters (such as the wash-in rate and the wash-out rate) allows detecting the lesions by localizing regions in the body-part with high values of these wash-in and wash-out rates. However, reliable parametric analyses generally require images that are spatially sub-sampled—i.e. pixel values of groups of neighboring pixels are low-pass filtered and then sub-sampled (according to a sub-sampling factor) to produce cell values for corresponding cells, on which the fitting operation is then performed. In this way, it is possible to increase a signal-to-noise ratio (SNR)—normally very low in the original echo signals—and to reduce a computation time—normally very high because of the complexity of the fitting operation and the large number of pixels. However, spatial sub-sampling generates parametric images with degraded resolution (which is not optimal for the characterization of the lesions). Moreover, echo signals must be recorded over an extended duration (encompassing the wash-in phase and a substantial part of the wash-out phase) in order to guarantee an acceptable robustness of the fitting operation (and then to provide reliable perfusion parameter estimates). Therefore, the echo signals are usually processed off-line (with a post-processing time that can easily exceed 3-8 minutes); proceeding in this way prevents any real-time examination of the body-part.

Imaging analyses may instead be used to characterize the lesions. Indeed, the examination of the images representing blood perfusion in the body-part (at full resolution) is useful to determine its vascular properties. However, identification of tiny blood vessels (such as capillaries) is challenging because the local contrast agent concentration can be very low (with blood vessels that may even contain only a single contrast agent microbubble as they are being imaged).

In order to solve this problem, a solution known in the art involves the application of a Maximum Intensity Projection (MIP) algorithm to the images (for example, as disclosed in U.S. Pat. No. 6,676,606, the entire disclosure of which is incorporated herein by reference). Particularly, for each pixel the maximum intensity projection algorithm holds the corresponding values in the different images to their maximum over time. In this way, trajectories of contrast agent particles are projected spatially, so as to emphasize the corresponding blood vessel morphology. However, in this way the images become diffuse as soon as the contrast agent starts perfusing the parenchymal tissue surrounding the lesions; therefore, the representation of the vascular properties of the lesions gets blurred and loses conspicuity (thereby considerably reducing the effectiveness of the imaging analyses for lesion characterization).

A Minimum Intensity Projection (mIP) algorithm is also known in the art; in this case, for each pixel the minimum intensity projection algorithm holds the corresponding values in the different images to their minimum over time. The minimum intensity projection algorithm may be used before contrast agent arrival in the images to suppress background clutter and improve the visualization of the contrast agent (for example, as suggested in U.S. Pat. No. 6,436,049, the entire disclosure of which is incorporated herein by reference); however, this algorithm is completely ineffective with respect of the above-mentioned problems.

It should be noted that the imaging analyses based on the maximum intensity projection algorithm might also be used to perform a qualitative detection of the lesions—e.g., in locations of the body-part that exhibit an early enhancement of the contrast agent during the wash-in phase. However, the maximum values of the echo signals for the lesions and the parenchymal tissue may be similar, so that their representations after application of the maximum intensity projection algorithm become similar at times after reaching their corresponding peaks; therefore, this approach is useful to emphasize differences in the perfusion kinetics only during the short period of the wash-in phase. In any case, any information about the wash-out phase is completely lost (since the pixel values remain constant after reaching their peaks).

SUMMARY

In its general terms, the solution according to an embodiment of the present invention is based on the idea of using signal monitoring techniques.

Particularly, an aspect of the present invention proposes a diagnostic system (for example, an ultrasound scanner or a computer associated therewith). The system includes means for providing a plurality of input signals; the input signals represent a body-part that is perfused with a contrast agent over time. Particularly, each input signal is indicative of a response to an interrogating stimulus of a corresponding location of the body-part that possibly includes the contrast agent (for example, an echo signal from ultrasound pulses). The system also includes means for generating a plurality of filtered signals from selected input signals of selected locations (for example, in a region of interest); each filtered signal at each instant over time is generated from a corresponding selected input signal according to a portion of the selected input signal including said instant (for example, by applying a maximum intensity projection algorithm). In the solution according to an embodiment of the invention, means is provided for monitoring each filtered signal to detect a peak in the response to the interrogating stimulus of the corresponding selected location; the peak is detected when a stability condition is fulfilled by a corresponding portion of the filtered signal (for example, when the filtered signal remains constant for a predefined period).

In an embodiment of the invention, the means for monitoring each filtered signal includes means for verifying the stability condition over time at a set of monitoring instants (for example, at each acquisition instant of the corresponding input signal); the verification is stopped after the stability condition has been fulfilled. Means is then provided for detecting the peak according to the monitoring instant at which the stability condition is fulfilled.

In an embodiment of the invention, the system includes means for verifying (at each monitoring instant) whether the filtered signal remained constant in a stability time-window preceding the monitoring instant; the system then includes means for detecting the peak at an instant preceding the monitoring instant at which the stability condition is fulfilled by the stability time-window.

In an embodiment of the invention, the system further includes means for calculating one or more perfusion parameters—indicative of the perfusion of each selected location—according to the corresponding peak (for example, a wash-in rate).

In an embodiment of the invention, the system includes means for generating a linearized input signal from each selected input signal; the linearized input signal at each instant is substantially proportional to a concentration of the contrast agent in the corresponding selected location at said instant. The system also includes means for calculating each perfusion parameter according to the corresponding linearized input signal, at one or more instants that are determined by the means for monitoring.

In an embodiment of the invention, the system includes means for providing a sequence of input images. Each input image includes a digital representation of the body-part at a corresponding instant; particularly, each input image includes a plurality of input values each one indicative of the response to the interrogating stimulus of a corresponding location at the corresponding instant. The system also includes means for generating a sequence of filtered images from the input images. For each selected location, each filtered image includes a filtered value that is generated according to the input values corresponding to the selected location in a set of selected input images; the set of selected input images consists of a corresponding input image and one or more preceding input images. In this case, the system includes means for monitoring the filtered values of each selected location.

In an embodiment of the invention, the system includes means for setting each filtered value of each filtered image to a value, which is representative of a maximum response to the interrogating stimulus of the corresponding selected location in the selected input images until the corresponding peak has been detected (for example, it is obtained by applying a maximum intensity projection algorithm); optionally, the filtered value may be also representative of a minimum response to the interrogating stimulus of the corresponding selected location in the selected input images after the corresponding peak has been detected (for example, it is now obtained by applying a minimum intensity projection algorithm).

In an embodiment of the invention, the system includes means for setting the filtered value to a value that is representative of the maximum response to the interrogating stimulus between the filtered value of the selected location in a preceding filtered image and a comparison value until the corresponding peak has been detected; the comparison value is based on a set of input values of the selected location in a set of comparison input images (including the corresponding input image). Optionally, the filtered value may also be set to a value, which is representative of the minimum response to the interrogating stimulus between the filtered value of the selected location in the preceding filtered image and the comparison value after the corresponding peak has been detected.

In an embodiment of the invention, the comparison value consists of the input value of the selected location in the corresponding input image. In an alternative embodiment of the invention, the comparison input images consist of the corresponding input image and one or more preceding input images; in this case, the system includes means for calculating the comparison value by applying a smoothing function to the input values of the selected location in the comparison input images (for example, a median function).

In an embodiment of the invention, the system further includes means for generating one or more sequences of dynamic parametric images; for each selected location, each dynamic parametric image includes a null value before a corresponding perfusion parameter is calculated, and a value that is indicative of the corresponding perfusion parameter after its calculation (for example, in a color-coded representation).

In an embodiment of the invention, the system includes means for maintaining the null value for each selected location of each dynamic parametric image even after the calculation of the corresponding perfusion parameter, when this perfusion parameter does not reach a threshold value.

In an embodiment of the invention, the system further includes means for generating a sequence of overlaid images for each sequence of dynamic parametric images; the overlaid images are generated by overlaying each dynamic parametric image on a corresponding filtered image.

In an embodiment of the invention, the system includes means for detecting an arrival instant (which is indicative of an instant at which the filtered signal reaches a significant value), and means for detecting a peak instant (which is indicative of an instant of detection of the peak); the system then includes means for determining a peak value, which is indicative of a response to the interrogating stimulus of the corresponding selected location at the peak instant. Optionally, the system may also include means for detecting a reduction instant, which is indicative of an instant at which the filtered signal reaches a reduction value—with the reduction value being a predefined fraction of the peak value (for example, a half-peak value).

In an embodiment of the invention, the system includes means for calculating a wash-in rate (according to a ratio between the peak value and a difference between the peak instant and the arrival instant), means for calculating a wash-out rate (according to a ratio between the reduction value and a difference between the reduction instant and the peak instant), means for calculating a product between the wash-in rate and the wash-out rate, or any other mathematical combination thereof.

In an embodiment of the invention, the system further includes means for applying a destruction pulse to the body-part (so as to cause a substantial destruction of the contrast agent); the system then includes means for repeating one or more times an actuation of the means for performing the above-mentioned operations.

Another aspect of the present invention proposes a corresponding data processing method. Particularly, the data processing method includes the step of providing a plurality of input signals; the input signals represent a body-part that is perfused with a contrast agent over time. Each input signal is indicative of a response to an interrogating stimulus of a corresponding location of the body-part that possibly includes the contrast agent. The method also includes the step of generating a plurality of filtered signals from selected input signals of selected locations; each filtered signal at each instant over time is generated from a corresponding selected input signal according to a portion of the selected input signal including said instant. In the solution according to an embodiment of the invention, each filtered signal is monitored to detect a peak in the response to the interrogating stimulus of the corresponding selected location; the peak is detected when a stability condition is fulfilled by a corresponding portion of the filtered signal.

The same additional features described above with reference to the diagnostic system apply mutatis mutandi to the data processing method (either alone or in combination with each other).

A further aspect of the present invention proposes a corresponding computer program. Particularly, the computer program includes code means for causing a data processing system to perform the steps of the above-mentioned data processing method when the computer program is executed on the system.

A still further aspect of the present invention proposes a corresponding computer program product. Particularly, the computer program product includes a computer-usable medium embodying a computer program, the computer program when executed on a data processing system causing the system to perform the same data processing method.

BRIEF DESCRIPTION OF THE DRAWINGS

The solution according to one ore more embodiments of the invention, as well as further features and the advantages thereof, will be best understood with reference to the following detailed description, given purely by way of a non-restrictive indication, to be read in conjunction with the accompanying drawings, in which:

FIG. 2A-2B illustrate an exemplary application of the solution according to an embodiment of the invention, FIG. 7A-7D show an example of in-vivo application of the solution according to an embodiment of the invention compared with techniques known in the art, FIG. 8A-8C show another example of in-vivo application of the solution according to an embodiment of the invention compared with techniques known in the art.

DETAILED DESCRIPTION

Figure 1:
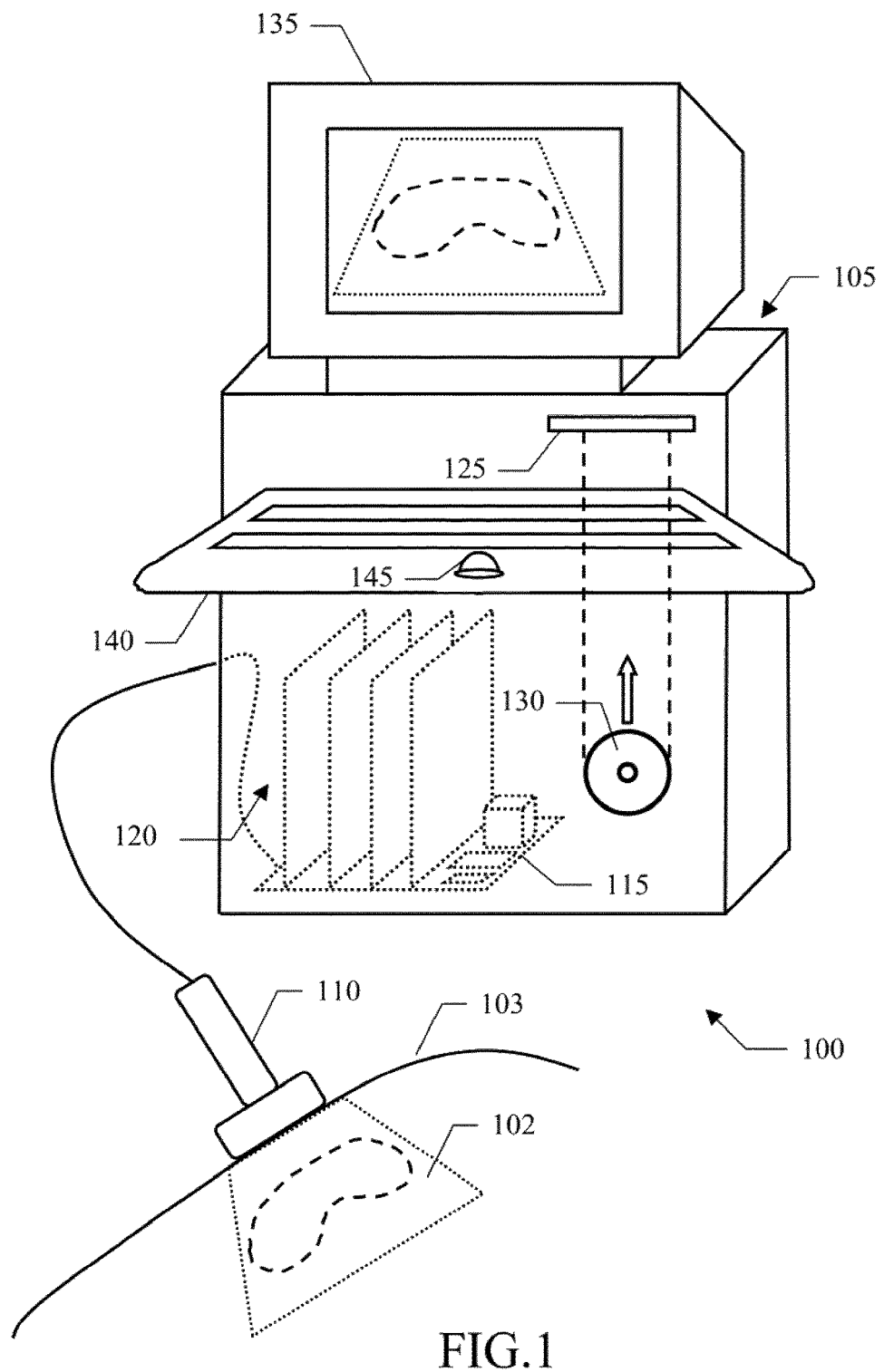
FIG. 1 is a pictorial representation of a medical imaging system in which the solution according to an embodiment of the invention is applicable.

With reference in particular to FIG. 1, a medical imaging system consisting of an ultrasound scanner 100 is illustrated; the scanner 100 may be used to analyze a body-part 102 of a patient 103 in the solution according to an embodiment of the invention. The ultrasound scanner 100 includes a central unit 105 and a hand-held transmit-receive imaging probe 110 (for example, of the array type). The imaging probe 110 transmits ultrasound waves consisting of a sequence of pulses (for example, having a center frequency between 1 and 50 MHz), and receives radio-frequency (RF) echo signals resulting from the reflection of the ultrasound pulses by the body-part 102; for this purpose, the imaging probe 110 is provided with a transmit/receive multiplexer, which allows using the imaging probe 110 in the above-described pulse-echo mode.

The central unit 105 houses a motherboard 115, on which the electronic circuits controlling operation of the ultrasound scanner 100 (for example, a microprocessor, a working memory and a hard-disk drive) are mounted. Moreover, one or more daughter boards (denoted as a whole with 120) are plugged into the motherboard 115; the daughter boards 120 provide the electronic circuits for driving the imaging probe 110 and for processing the received echo signals. The ultrasound scanner 100 can also be equipped with a drive 125 for reading removable disks 130 (such as CD-ROMs or DVD-ROMs). A monitor 135 displays images relating to an analysis process that is in progress. Operation of the ultrasound scanner 100 is controlled by means of a keyboard 140, which is connected to the central unit 105 in a conventional manner; preferably, the keyboard 140 is provided with a trackball 145 that is used to manipulate the position of a pointer (not shown in the figure) on a screen of the monitor 135.

During the analysis of the body-part 102, a contrast agent (acting as an efficient ultrasound reflector) is administered to the patient 103. For example, the contrast agent consists of a suspension of gas bubbles in a liquid carrier; typically, the gas bubbles have diameters on the order of 0.1-5 μm, so as to allow them to pass through the capillaries of the patient. The gas bubbles are generally stabilized by entraining or encapsulating the gas or a precursor thereof into a variety of systems, including emulsifiers, oils, thickeners, sugars, proteins or polymers; stabilized gas bubbles are generally referred to as gas-filled microvesicles. The microvesicles include gas bubbles dispersed in an aqueous medium and bound at the gas/liquid interface by a very thin envelope involving a surfactant, i.e., an amphiphilic material (also known as microbubbles). Alternatively, the microvesicles include gas bubbles that are surrounded by a solid material envelope formed of lipids or of natural or synthetic polymers (also known as microballoons or microcapsules). Another kind of contrast agent includes a suspension of porous microparticles of polymers or other solids, which carry gas bubbles entrapped within the pores of the microparticles. Examples of suitable aqueous suspensions of microvesicles, in particular microbubbles and microballoons, and of the preparation thereof are described in EP-A-0458745, WO-A-91/15244, EP-A-0554213, WO-A-94/09829 and WO-A-95/16467 (the entire disclosures of which are herein incorporated by reference). An example of a commercial contrast agent comprising gas-filled microvesicles is SonoVue® by Bracco International BV.

Preferably, the contrast agent is administered to the patient 103 intravenously as a bolus—i.e., a single dose provided by hand with a syringe over a short period of time (of the order of 2-20 seconds). The contrast agent circulates within a vascular system of the patient 103, so as to perfuse the body-part 102. At the same time, the imaging probe 110 is placed in contact with the skin of the patient 103 in the area of the body-part 102. The body-part 102 is then insonated by applying a series of ultrasound pulses with low acoustic energy (such as with a mechanical index MI=0.01-0.1), so as to involve a negligible destruction of the contrast agent (such as less than 5%, and preferably less than 1% of its local concentration between successive ultrasound pulses). The echo signals that are recorded in response to the ultrasound pulses over time (for each location of the body-part 102 in a selected scanning plan) provide a representation of a corresponding region (i.e., a slice) of the body-part 102—possibly including the contrast agent—during the analysis process.

The echo signals are then converted into a sequence of digital images (or frames) in standard Brightness mode (B-mode), which then represent the body-part 102 at corresponding successive acquisition instants (for example, with a frame rate FR=10-30 images per second). Each image is defined by a matrix (for example, with M=512 rows and N=512 columns) of values for respective visualizing elements—i.e., basic picture elements (pixels), each one corresponding to a location of the body-part 102. Typically, each pixel value consists of a gray-scale level (for example, coded on 8 bits) defining the brightness of the pixel; the pixel value increases from 0 (black) to 255 (white) as a function of the intensity of the corresponding echo signal (representing the acoustical response at the corresponding location of the body-part).

The echo signals and then the corresponding images generally result from the superimposition of different contributions generated by the contrast agent and the surrounding tissue. Preferably, the ultrasound scanner 100 operates in a contrast-specific imaging mode so as to substantially remove, or at least reduce, the dominant (linear) contribution of tissue in the echo signals, with respect to the (non-linear) contribution of the contrast agent; examples of contrast-specific imaging modes include harmonic imaging (HI), pulse inversion (PI), power modulation (PM) and contrast pulse sequencing (CPS) techniques, as described, for example, in "Rafter et al., Imaging technologies and techniques, Cardiology Clinics 22 (2004), pp. 181-197" (the entire disclosure of which is herewith incorporated by reference).

In FIG. 2A, a time-intensity curve 205 (solid-line) is shown as an exemplary response to the ultrasound waves of a generic location of the body-part—representing the power of the corresponding echo signal (in terms of arbitrary units, or a.u.) as a function of time (in seconds). The curve 205 has an initial portion wherein the echo signal increases from zero (before contrast agent arrival) towards a peak, as a result of a wash-in phase of the contrast agent perfusing the body-part after its administration; once the echo signal has reached its absolute maximum value at this peak, it starts decreasing towards zero as a result of a wash-out phase of the contrast agent that is filtered out of the patient (for example, by the lungs and/or by the liver).

The echo signal is at first filtered, so as to generate a filtered signal that is represented in the figure with a curve 210 (dashed-line). As described in detail in the following, at each instant the filtered signal is generated from the echo signal according to a corresponding portion of the echo signal including the same instant. For example, at the beginning the filtered signal is generated by applying the maximum intensity projection algorithm, wherein the echo signal is held at its maximum value over time. In this way, the corresponding portion of the curve 210 (denoted with 210*a*) accurately follows the curve 205 when the echo signal increases monotonously; however, if the echo signal momentarily decreases (for example, due to noise or natural fluctuation in local contrast agent concentration), its last maximum value is preserved until a higher value of the echo signal is detected.

The filtered signal can be generated at any instant simultaneously with the recording of the echo signal (or at most with a very short delay). For example, the maximum intensity projection algorithm only requires the knowledge of the echo signal up to the corresponding instant (so that the filtered signal can be generated in real-time according to information that is already available).

In the solution according to an embodiment of the invention, the filtered signal is subsequently monitored in order to detect its peak (at a peak instant $t_p$, when the filtered signal reaches a peak value $I_p$); particularly, the peak is detected when a corresponding portion of the filtered echo signal fulfills a stability condition. For example, this happens when the filtered signal remains constant for a predefined period. Therefore, the peak is now detected as soon as it occurs (with a short delay required for fulfilling the stability condition).

The filtering of the echo signal is relatively simple and does not require extensive computational resources, so that it can be performed at the pixel level (without any spatial sub-sampling of the images). Nevertheless, the filtered signal is significantly smoothed (by removing any strong variations of the corresponding echo signal before filtering), thereby allowing the detection of the peak in a robust way. As a result, the proposed processing can be performed at full image resolution with an acceptable degree of reliability.

At the same time, the proposed solution allows obtaining the desired results substantially in real-time; this means that the analysis process is being carried out while the body-part is being imaged—i.e., with a short delay from the detection of the peaks due to the required computations, but without the need of waiting for the imaging process to be completed.

In addition or in alternative, after the detection of the peak the filtering operation is switched to the minimum intensity projection algorithm, wherein the echo signal is held at its minimum value over time. In this way, the corresponding portion of the curve 210 (denoted with 210b) now accurately follows the curve 205 when the echo signal decreases monotonously (during the contrast agent wash-out phase); however, if the echo signal momentarily increases (due to noise or natural fluctuations in the contras agent concentration), its last minimum value is preserved until a lower value of the echo signal is detected.

In this way, information about the wash-out phase is preserved as well. At the same time, further examinations of the body-part may be performed again on full-resolution images and substantially in real-time.

Figure 2B:
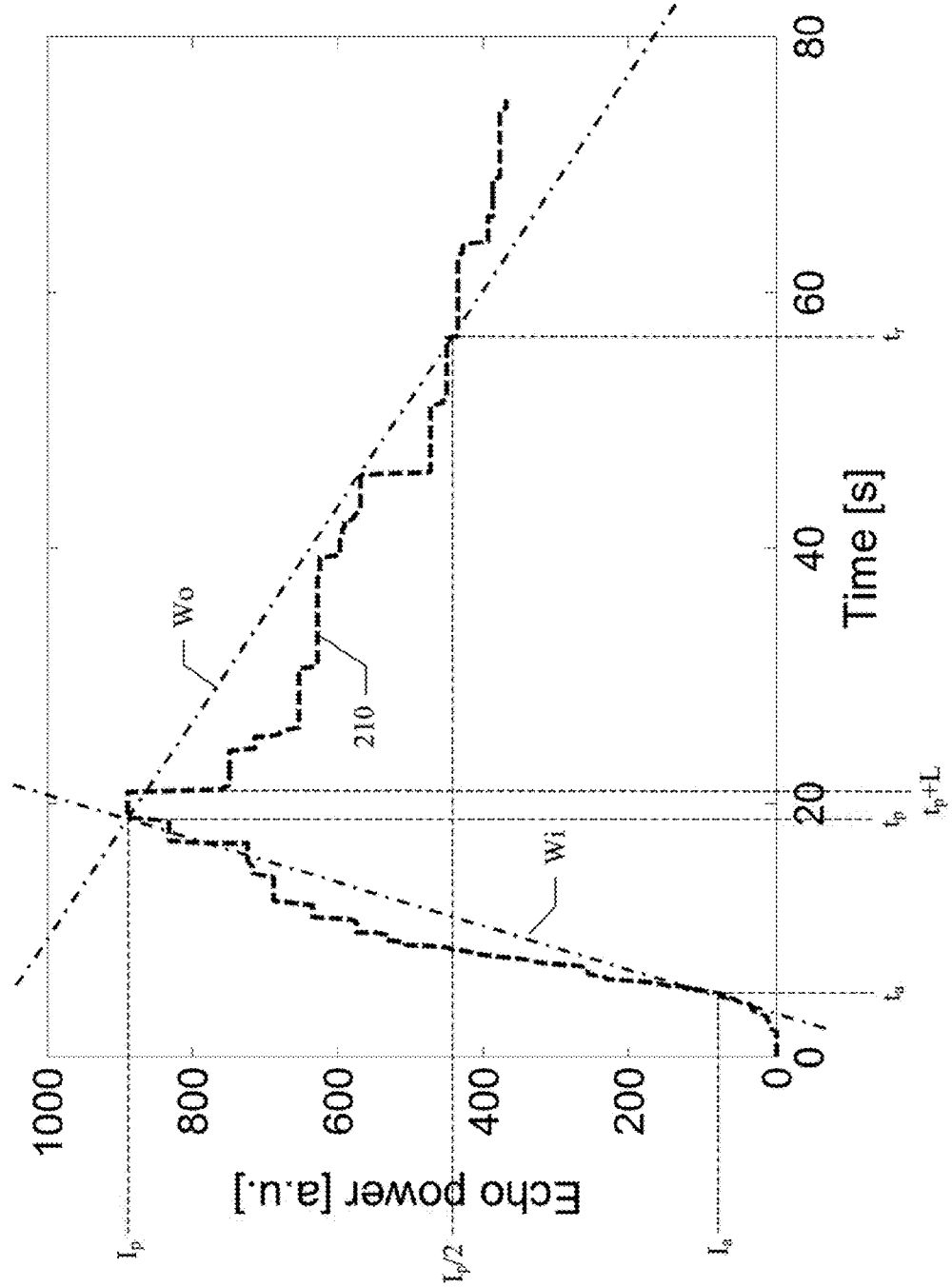

The information relating to the detection of the peak can be used for different purposes. Particularly, as shown in FIG. 2B, in an embodiment of the invention, this information is used to calculate one or more perfusion parameters (indicative of the blood perfusion in the corresponding location of the body-part). For example, it is possible to calculate a wash-in rate Wi (as represented in FIG. 2B by a corresponding dashed-dotted straight line) using the following formula:

$$Wi = \frac{I_p}{\Delta t_i},$$

wherein $\Delta t_i = t_p - t_a$ measures a duration of the wash-in phase (from a contrast agent arrival instant $t_a$ to the peak instant $t_p$). The arrival instant $t_a$ is defined as the instant at which the filtered signal reaches a significant value $I_a$ exceeding a predefined threshold value. It should be noted that this wash-in rate Wi is very reliable, since it is completely independent of the instant of the contrast agent administration.

In addition or in alternative, the filtered signal is also monitored to detect a half-peak instant $t_r$, wherein the filtered signal falls to under a half-peak value $I_p/2$. It is then possible to calculate a wash-out rate Wo (as represented in FIG. 2B by a corresponding dashed-dotted straight line) using the following formula:

$$Wo = \frac{I_p/2}{\Delta t_o},$$

wherein $\Delta t_o = t_r - t_p$ measures a duration of the wash-out phase (from the peak instant $t_p$ to the half-peak instant $t_r$). In this case as well, the wash-out rate Wo is very reliable, since it is again independent of the instant of the contrast agent administration.

In an embodiment of the invention, the above-described method is used to generate a sequence of filtered images from the (original) images representing the body-part. Particularly, for each pixel the corresponding pixel values in the different filtered images are obtained by applying the maximum intensity projection algorithm before their peak instant $t_p$ and the minimum intensity projection algorithm afterward.

More formally, before the peak instant $t_p$, each pixel value of the filtered images is set to the maximum between the pixel value for the same pixel in the corresponding original image and the running maximum of the pixel values for the same pixel in the preceding original images as resulting from the earlier iterations of the process, that is:

$$OP(x,y,k) = \text{MAX}[IP(x,y,k), OP(x,y,k-1)],$$

wherein $OP(x,y,k)$ is the pixel value of the pixel identified by the spatial coordinates x,y (row number and column number, respectively) in the filtered image with number k (taken at an instant t being the inverse of the frame rate of the original images multiplied by the image number k—i.e., t=k/FR). $IP(x,y,k)$ and $OP(x,y,k-1)$ are the pixel values of the same pixel (x,y) in the corresponding original image with the same number k (taken at the instant t) and in the preceding filtered image with the number k-1 (taken at the instant (k-1)/FR), respectively, and MAX[ ] is a function returning the maximum value among its arguments. After the peak instant $t_p$, instead, each pixel value of the filtered images is set to the minimum between the pixel value for the same pixel in the corresponding original image and the running minimum of the pixel values for the same pixel in the preceding original images (from the peak forward) as resulting from the earlier iterations of the process, that is:

$$OP(x,y,k) \text{MIN}[IP(x,y,k), OP(x,y,k-1)],$$

wherein MIN[ ] is a function returning the minimum value among its arguments.

In general, each pixel value of the filtered images can then be calculated by applying the following filtering function:

$$OP(x, y, k) = \begin{cases} \text{MAX}[IP(x, y, k), OP(x, y, k-1)] & \text{if } k \le k_p + L \\ \text{MIN}[IP(x, y, k), OP(x, y, k-1)] & \text{if } k > k_p + L, \end{cases}$$

wherein L (with L>0) is a stability length, which represents a number of filtered images that are used to detect the peak, and $k_p$ (with $k_p$>L) is a peak number that expresses the peak instant $t_p$ in terms of image number (with $t_p = k_p/FR$). Particularly, the peak number $k_p$ is set to the image number k that satisfies the stability condition defined by:

$$k_p = k \text{ for } OP(x,y,k) - OP(x,y,k+L-1) = 0.$$

In other words, the peak is detected as soon as the pixel values in the filtered images remain at the same value for a number of filtered images defined by the stability length L (i.e., in a stability time-window given by the product of the stability length L by the inverse of the frame rate of the original images). The value of the stability length L (and then the value of the stability time-window) is tuned according to the opposed requirements of high accuracy and fast response of the analysis process. Particularly, higher values of the stability length L allow avoiding false detections of the peak—when the corresponding echo signal momentarily increases (for example, for durations corresponding to 1 or 2 original images only), with the resulting filtered signal that exhibits flat portions until the echo signal starts increasing again; however, increasing the stability length L delays the instant at which the peak is detected. For example, typical values of the stability length L are 3-12 (corresponding to a stability time-window of 0.3-1.2 s for a frame rate of 10 original images per second).

Figure 3A:
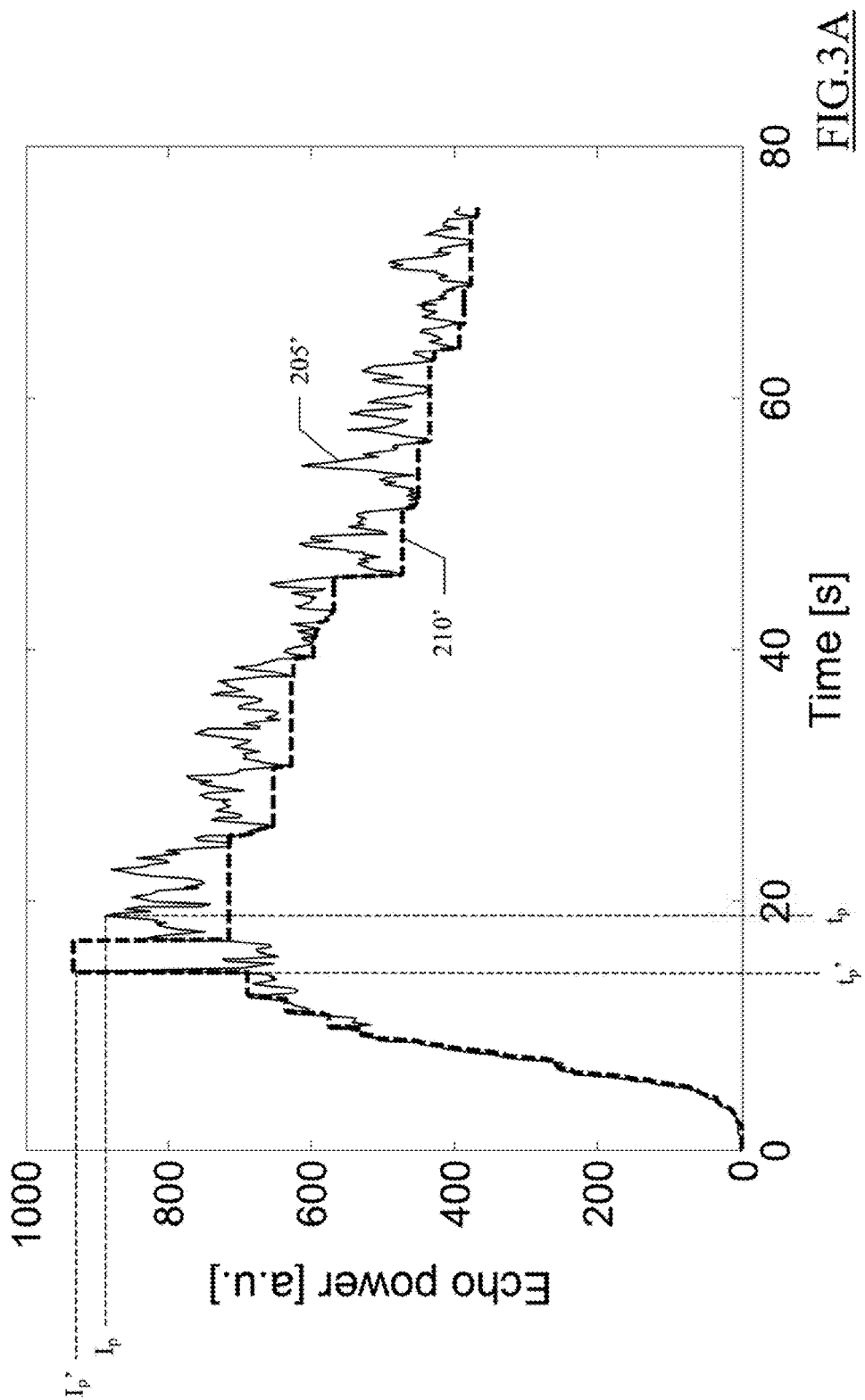
FIG. 3A-3B illustrate an exemplary application of the solution according to a further embodiment of the invention.

The above-described filtering algorithm (although providing reliable perfusion parameters in most practical situations) might show some limitations in critical conditions (for example, when the echo signal exhibits a very low SNR), as illustrated for instance in FIG. 3A. Particularly, when the echo signal—represented with a curve 205'—momentarily increases (spurious positive spike) during the wash-in phase or momentarily decreases (spurious negative spike) during the wash-out phase (for example, due to a motion artifact), the filtered signal—represented with a curve 210'—does not accurately follow the actual trend of the echo signal any longer. Indeed, for each positive spike the filtering algorithm holds the filtered signal at the spike value until the echo signal exceeds the held value; likewise, for each negative spike the filtering algorithm holds the filtered signal at the spike value until the echo signal drops to under the held value. The problem is particularly acute if a positive spike with a value higher than the peak value $I_p$ occurs before the peak instant $t_p$. In this case, a wrong peak would be detected at a peak instant $t_p' < t_p$ wherein the filtered signal reaches a peak value $I_p' > I_p$.

Figure 3B:
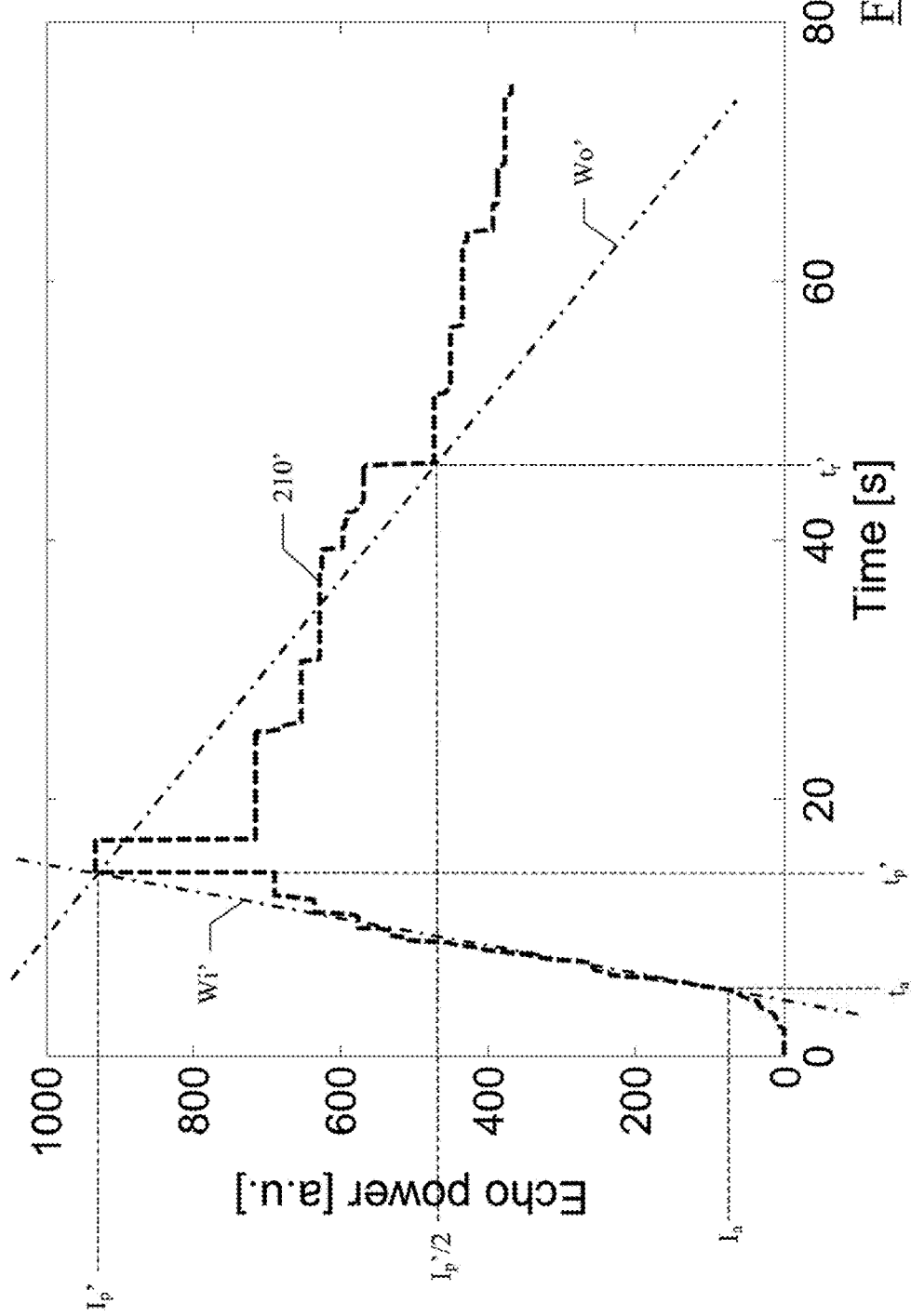

As shown in FIG. 3B, the error propagates to the calculation of the desired perfusion parameters (i.e., higher wash-in rate Wi', earlier half-peak instant $t_r'$ wherein the filtered signal reaches a higher half-peak value $I_p'/2$, and wrong wash-out rate Wo' in the example at issue). Similar considerations apply if a spurious negative spike occurs in the echo signal before the occurrence of the half-peak instant, during the wash-out phase, said negative spike having a value lower than the half-peak value.

However, the above-mentioned problem can be solved by smoothing the echo signal before filtering it according to the method mentioned before. With reference in particular to the wash-in phase, the running maximum of the pixel values is now compared with a smoothed value, which is based on a smoothing set of pixel values for the same pixel in the corresponding original image and in one or more preceding original images:

$$OP(x,y,k)=\text{MAX}[SP(x,y,k),OP(x,y,k-1)]$$

wherein SP(x,y,k) is the smoothed value for the pixel (x,y) in the original image with the number k. The smoothed value is in turn defined by applying a smoothing function on the smoothing set of pixel values:

$$SP(x,y,k)=\text{SMT}[IP(x,y,k) \ldots IP(x,y,k-m+1)],$$

wherein SMT[ ] is a smoothing function adapted to remove, or at least reduce, short (positive or negative) spikes in the smoothing set of pixel values, and m (with m≥2) is a smoothing length representing a number of the pixel values in the smoothing set (and then the number of the corresponding original images)—corresponding to a smoothing time-window given by the product of the smoothing length m by the inverse of the frame rate of the original images. A typical example of smoothing function well suited to this purpose is the median function (wherein the smoothed value represents the middle value in the set of smoothing pixel values arranged in ascending order). The value of the smoothing length m is tuned according to the opposed requirements of high accuracy and fast response of the analysis process. Particularly, higher values of the smoothing length m allow removing spikes with a longer duration in the corresponding echo signal (lasting up to half the smoothing time-window); however, increasing the smoothing length m delays the instant at which the (smoothed) images are available for filtering. For example, typical values of the smoothing length m are 2-6 (corresponding to a smoothing time-window of 0.2-0.6 s for the same frame rate of 10 original images per second).

The same smoothing algorithm can also be applied to the wash-out phase. In this case, the running minimum of the pixel values is likewise compared with the smoothed value (based on the same smoothing set of pixel values):

$$OP(x,y,k)\text{MIN}[SP(x,y,k),OP(x,y,k-1)].$$

Therefore, the whole filtering function now becomes:

$$OP(x, y, k) = \begin{cases} \text{MAX}[SP(x, y, k), OP(x, y, k-1)] & \text{if } k \leq k_p + L \\ \text{MIN}[SP(x, y, k), OP(x, y, k-1)] & \text{if } k > k_p + L. \end{cases}$$

The above-described solution also allows analyzing multiple regions of the body-part with a single bolus injection of the contrast agent. Indeed, the analysis process completes once the desired perfusion parameters have been calculated (i.e., after the peak instant for the wash-in rate or after the half-peak instant for the wash-out rate). However, a substantial amount of contrast agent may still be circulating in the patient; for example, in a typical application the peak is detected after 30-40 s, while the wash-out phase ends only after 60-90 s.

Figure 4A:
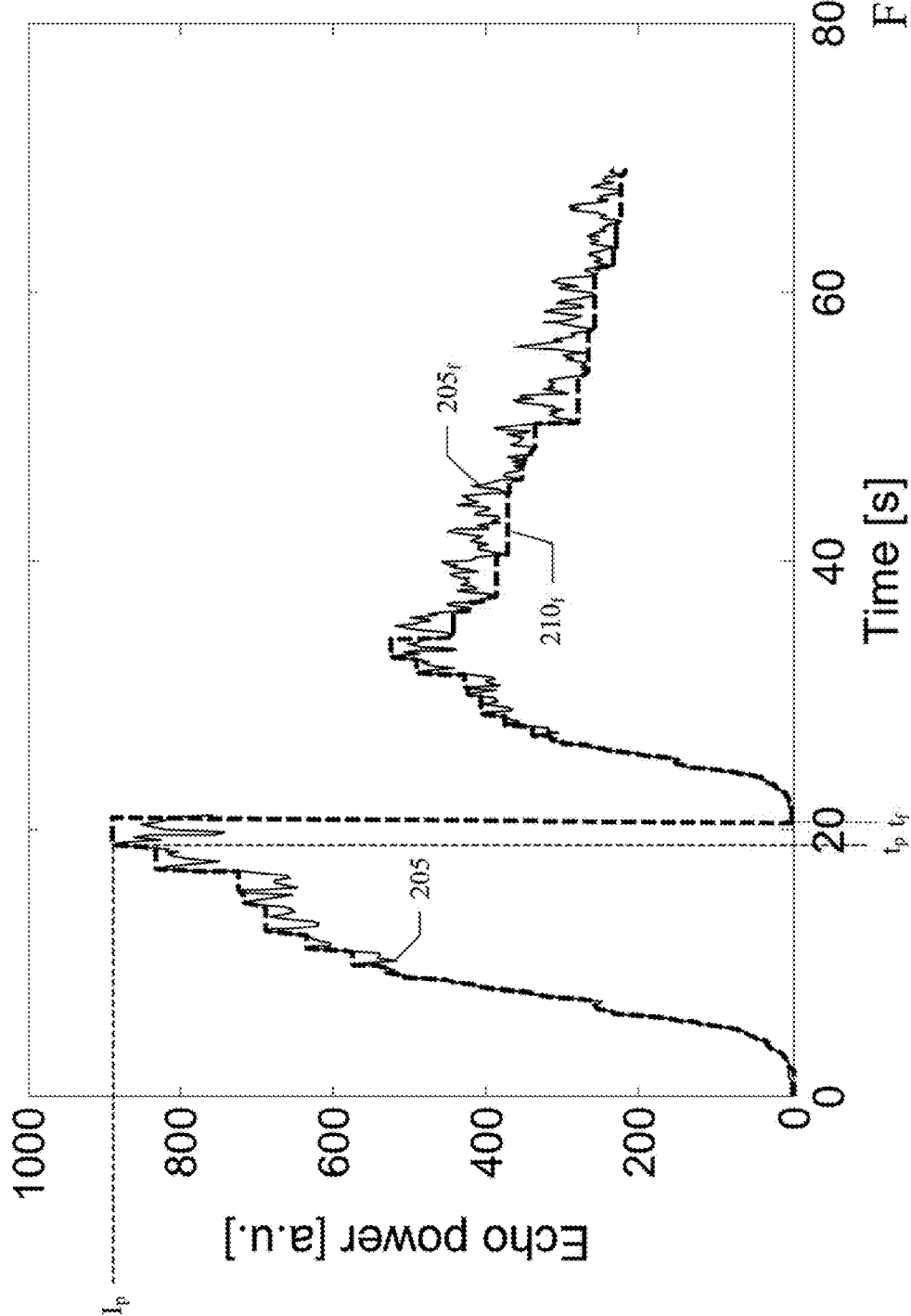
FIG. 4A-4B illustrate an exemplary application of the solution according to a still further embodiment of the invention, FIG. 5A-5A' and FIG. 5B-5B' show an exemplary scenario of application of the solution according to an embodiment of the invention.

Therefore, as shown in FIG. 4A, it is possible to destroy the remaining circulating contrast agent by applying one or more ultrasound pulses with high acoustic energy (flash) to the body-part as soon as the information required to calculate the desired perfusion parameters has been obtained (for example, at a flash instant $t_f > t_p + L$ after the wash-in rate Wi has been calculated); the acoustic energy must be sufficient (such as with a mechanical index of 1-2) to cause the destruction of a substantial amount of the remaining circulating contrast agent (for example, at least 50% of its local concentration before the application of the flash). The circulating contrast agent then replenishes the body-part. Therefore, if the imaging probe is moved to another scanning plane, the echo signals that are recorded after the flash instant $t_f$ represent a re-perfusion of another relevant region of the body-part. Particularly, a new echo signal of a generic location of the body-part now under analysis is represented with a curve $205_r$, which has a pattern similar to the one of the curve 205 for the (original) echo signal (i.e., increasing from zero towards a lower peak during a new wash-in phase, and then decreasing towards zero during a new wash-out phase). The same operations described above (i.e., filtering the new echo signal to obtain a new filtered signal represented with a curve $210_f$, monitoring the new filtered signal to detect its peak, and calculating one or more perfusion parameters based thereon) can then be repeated for this location of the body-part.

Figure 4B:
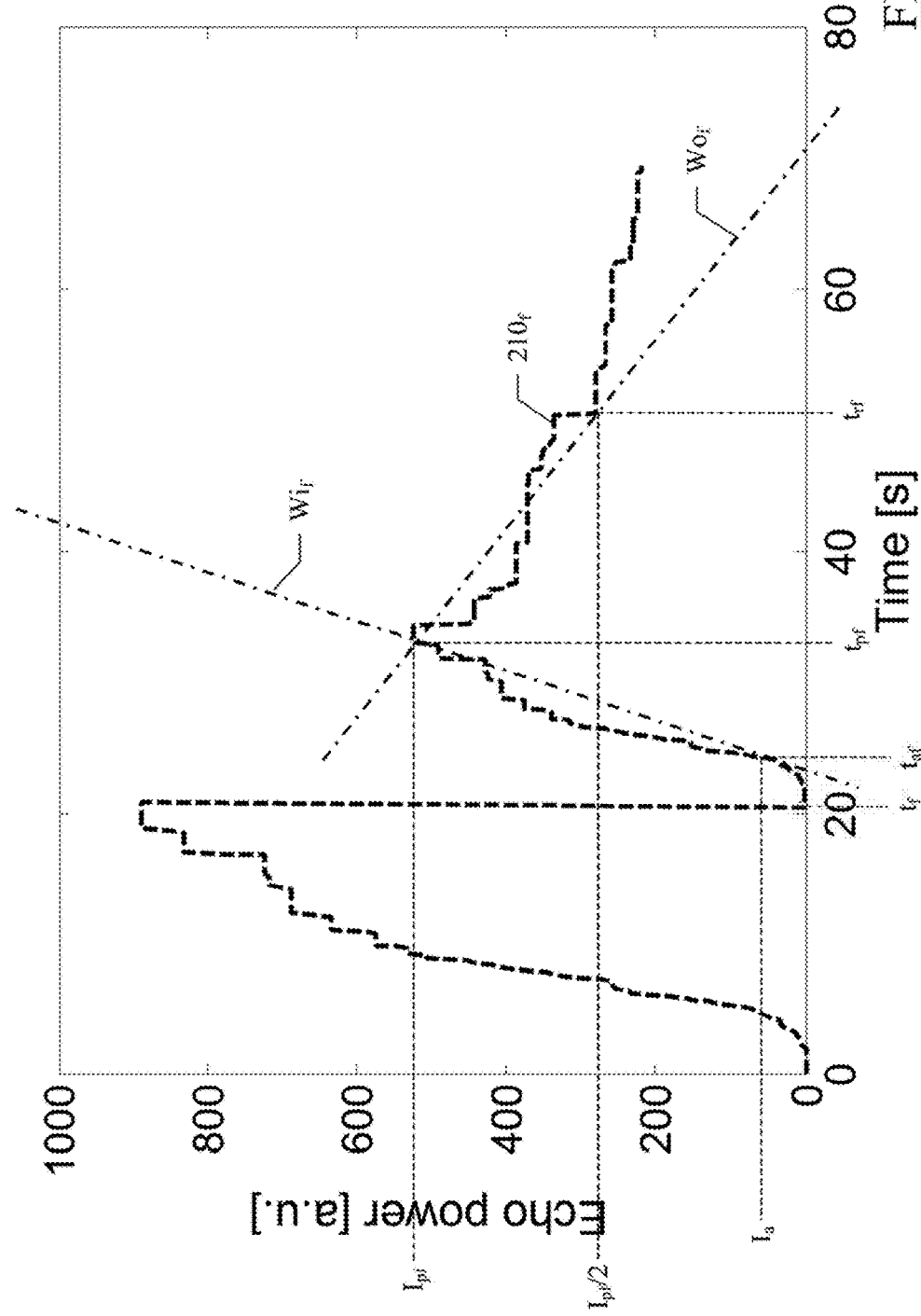

For example, as shown in FIG. 4B, it is possible to detect a new arrival instant $t_{af}$ (immediately after the destruction of the contrast agent), and a new peak instant $t_{pf}$ with a new peak value $I_{pf}$, in order to calculate a new wash-in rate $$Wi_f = \frac{I_{pf}}{\Delta t_{if}}$$

(with $\Delta t_{if} = t_{pf} - t_{af}$); in addition or as an alternative, it is also possible to detect a new half-peak instant $t_{rf}$ when the filtered signal falls to under a new half-peak value $I_{pf}/2$, in order to calculate a new wash-out rate $$Wo_f = \frac{I_{pf}/2}{\Delta t_{of}},$$

(with $\Delta t_{of} = t_{rf} - t_{pf}$). Of course, the same process may be reiterated one or more times (as long as a sufficient amount of contrast agent remains circulating in the patient).

Figure 5A:
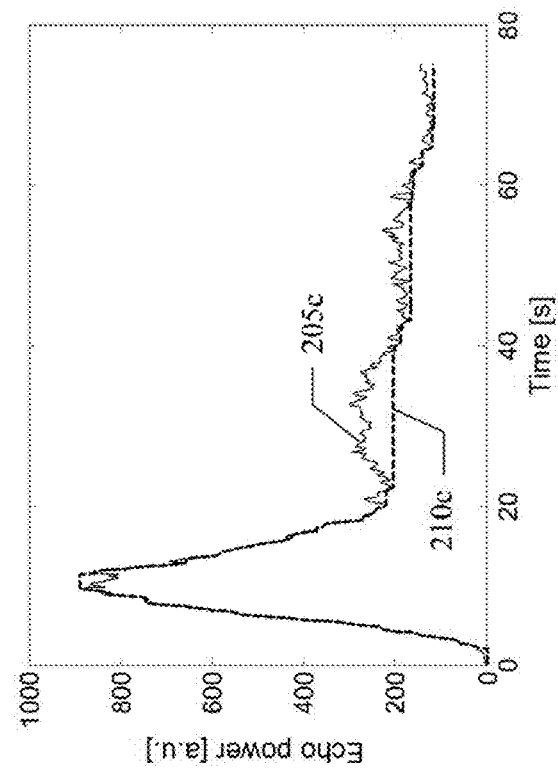
Figure 5A:
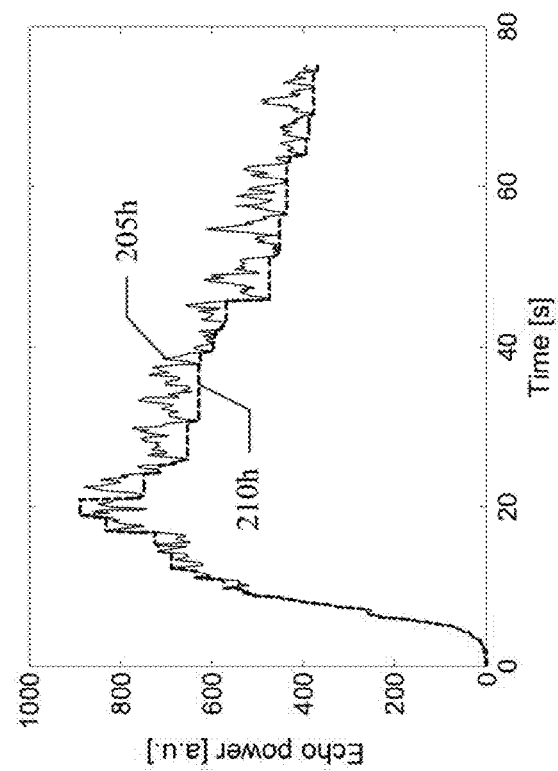

The above-described solution is particularly advantageous for prostate cancer diagnosis. Indeed, as shown in FIG. 5A-FIG. 5A', the echo signals relating to healthy (parenchymal) tissue and prostate cancer have a significant different pattern. Particularly, FIG. 5A shows the echo signal (represented with a curve $205_h$) and the corresponding filtered echo signal (represented with a curve $210_h$) of a location relating to healthy tissue; FIG. 5A' instead shows the echo signal (represented with a curve $205_c$ and the corresponding filtered echo signal (represented with a curve $210_c$) of a location affected by cancer. As can been seen, the echo signal of cancerous tissue (FIG. 5A') exhibits an earlier and faster wash-in and wash-out, as compared to the echo signal of healthy tissue (FIG. 5A).

Figure 5B:
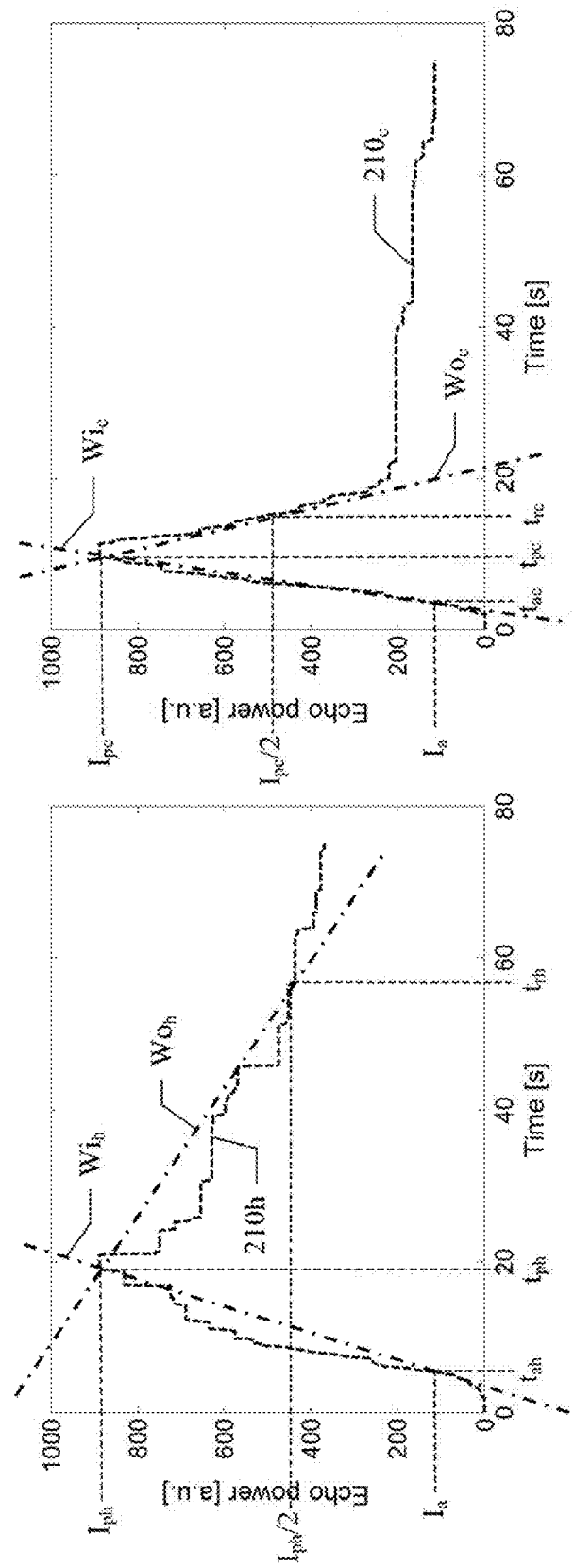

Therefore, as shown in FIG. 5B, the application of the proposed solution to healthy tissue allows detecting its peak at a peak instant $t_{ph}$ with a peak value $I_{ph}$; it is also possible to detect its arrival instant $t_{ah}$ and half-peak instant $t_{rh}$, so as to calculate a wash-in rate $$Wi_h = \frac{I_{ph}}{\Delta t_{ih}} = 53$$

(with $\Delta_{ih} = t_{ph} - t_{ah}$) and a wash-out rate $$Wo_h = \frac{I_{ph}/2}{\Delta t_{oh}} = 12$$

(with $\Delta t_{oh} = t_{rh} - t_{ph}$). Likewise, as shown in FIG. 5B', the application of the proposed solution to cancerous tissue allows detecting its peak at a peak instant $t_{pc}$ with a peak value $I_{pc}$; it is also possible to detect its arrival instant $t_{ac}$ and half-peak instant $t_{rc}$, so as to calculate a wash-in rate $$Wi_c = \frac{I_{pc}}{\Delta t_{ic}} = 118$$

(with $\Delta t_{ic} = t_{pc} - t_{ac}$) and a wash-out rate $$Wo_c = \frac{I_{pc}/2}{\Delta t_{oc}} = 72$$

(with $\Delta t_{oc} = t_{rc} - t_{pc}$). As can be seen, cancerous tissue can be easily differentiated from healthy tissue, since it provides a higher wash-in rate and a higher wash-out rate (i.e., $Wi_c=118$ and $Wo_c=72$ against $Wi_h=53$ and $Wo_h=12$, respectively).

As a further improvement, it is possible to combine the wash-in rate and the wash-out rate into a new perfusion parameter given by their product. This product for healthy tissue and for cancerous tissue is then $W_h=Wi_h \cdot Wh_o=53 \cdot 12=639$ and $W_c=Wi_c \cdot Wh_c=118 \cdot 72=8,469$, respectively. The devised new perfusion parameter further facilitates the differentiation of cancerous tissue from healthy tissue, since their differences are enhanced in the wash-in/wash-out rate products ($W_c=8,469$ against $W_h=639$).

More generally, the proposed solution facilitates the task of a physician, by providing intermediate results that may help him/her in performing the desired diagnosis (even though the diagnosis for curative purposes stricto sensu is always made by the physician himself/herself).

It should be noted that the above-described results could not be obtained by applying the maximum intensity projection algorithm or the minimum intensity projection algorithm alone.

Figure 6A:
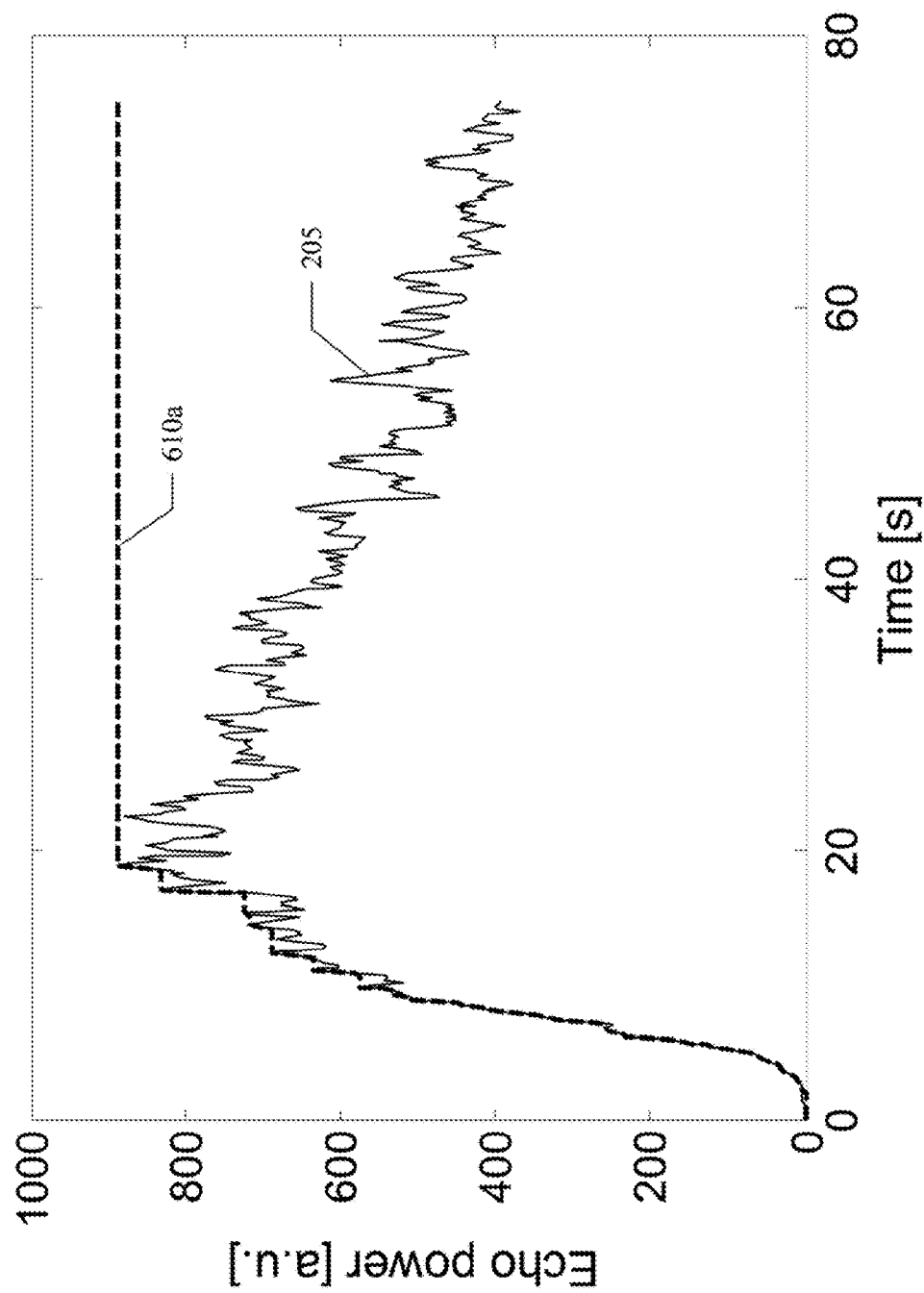
FIG. 6A-6B illustrate an exemplary application of a maximum intensity projection algorithm and of a minimum intensity projection algorithm known in the art, respectively.

Particularly, FIG. 6A illustrates the application of the maximum intensity projection algorithm alone to the same echo signal shown in FIG. 2A (again represented with the curve 205). In this case, the operation generates a filtered signal that is now represented with a curve 610a (dashed-line). As above, the curve 610a accurately follows the curve 205 until it reaches the peak of the echo signal (by filtering any strong variations in the echo signal); however, after the peak instant, the filtered signal now maintains its maximum value, so that the curve 610a remains constant. Therefore, any information about the wash-out phase is completely lost.

Figure 6B:
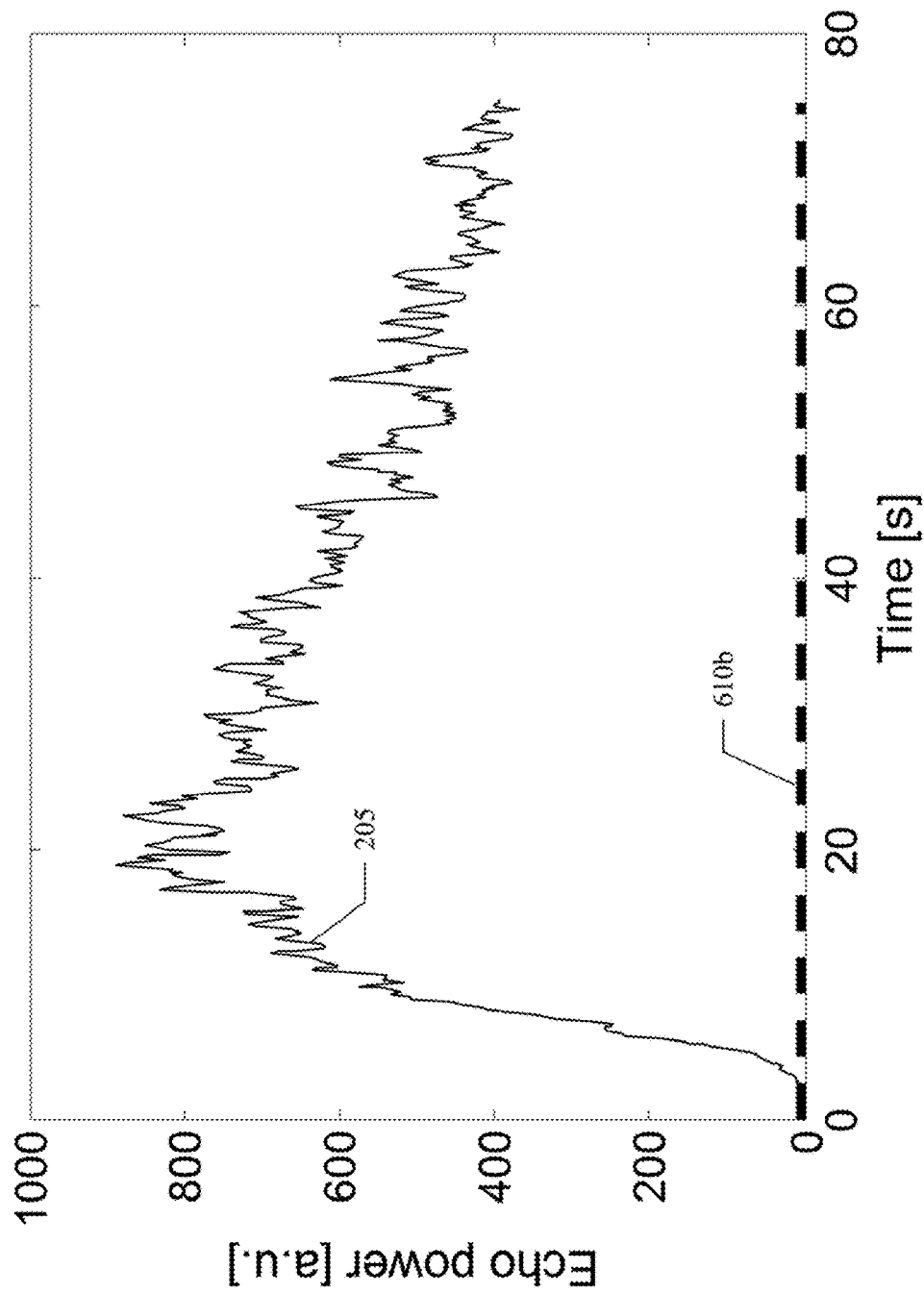

FIG. 6B instead illustrates the application of the minimum intensity projection algorithm alone to the same echo signal shown in FIG. 2A (again represented with the curve 205). In this case, the operation generates a filtered signal that is now represented with a curve 610b (dashed-line). As can be seen, the filtered signal always maintains its baseline value corresponding to the value before arrival of the contrast agent; as a result, the curve 610b is a simple horizontal line at this baseline value. Therefore, any information about the perfusion process (in both its wash-in phase and wash-out phase) is completely lost.

An example of in-vivo application of the solution according to an embodiment of the invention compared with techniques known in the art is shown in FIG. 7A-FIG. 7D. For this purpose, a human prostate was analyzed by means of a commercial ultrasound scanner after administering a bolus of the above-mentioned SonoVue® contrast agent.

Particularly, FIG. 7A shows a series of original images representing the prostate at different instants during the analysis process. The first image (A.1) relates to an early wash-in phase, the second image (A.2) relates to a late wash-in phase; the third image (A.3) relates to an early wash-out phase, and the fourth image (A.4) relates to a late wash-out phase. As shown in the images A.1 and A.2, during the wash-in phase, the contrast agent appears and enhances a highly vascularized central zone of the prostate, showing the typical symmetric enhancement of the contrast agent in this part thereof. Another region showing early contrast enhancement can be seen in the left peripheral zone of the prostate indicated by an arrow (i.e., on the lower-right side in the images). A region showing a similar pattern of contrast enhancement is instead absent in the contra-lateral part of the prostate—i.e., in the right peripheral zone of the prostate (on the lower-left side in the images). Such an asymmetric enhancement pattern, particularly in the peripheral zone of the prostate, is a typical indication of a suspicious region and may be related to a cancer. Moving to the image A.3, this typical early enhancement pattern in the suspicious region rapidly disappears when the wash-out in the suspicious region has started and the contrast agent begins perfusing the surrounding parenchymal tissue (the suspicious region becomes iso-echoic compared to the surrounding parenchymal tissue). Once the overall wash-out phase in the prostate has started (as shown in the image A.4), the typical enhancement pattern related to the suspicious region has disappeared and information about its location is completely lost.

FIG. 7B instead shows a series of maximum-hold images obtained by applying the maximum projection algorithm alone on the original images, such images (B.1, B.2, B.3 and B.4) being taken at the same instants as above. As shown in the images B.1 and B.2, the early enhancement of the contrast agent in the suspicious region remains visible during the whole wash-in phase (since the maximum value of each pixel is preserved over time even after the peak instant); therefore, the suspicious region is better defined and delineated as compared to the corresponding original images. Moreover, the images B.1 and B.2 also show the finest details of the microvascular network of the prostate (since the trajectories of the contrast agent are projected); this facilitates the examination of the suspicious region for its characterization. However, during the wash-out phase the images B.3 and B4 become diffuse; this is due to the enhancement of the surrounding parenchymal tissue, which reaches and maintains possibly similar maximum values, thus reducing the conspicuity of the suspicious region.

Figure 7C:
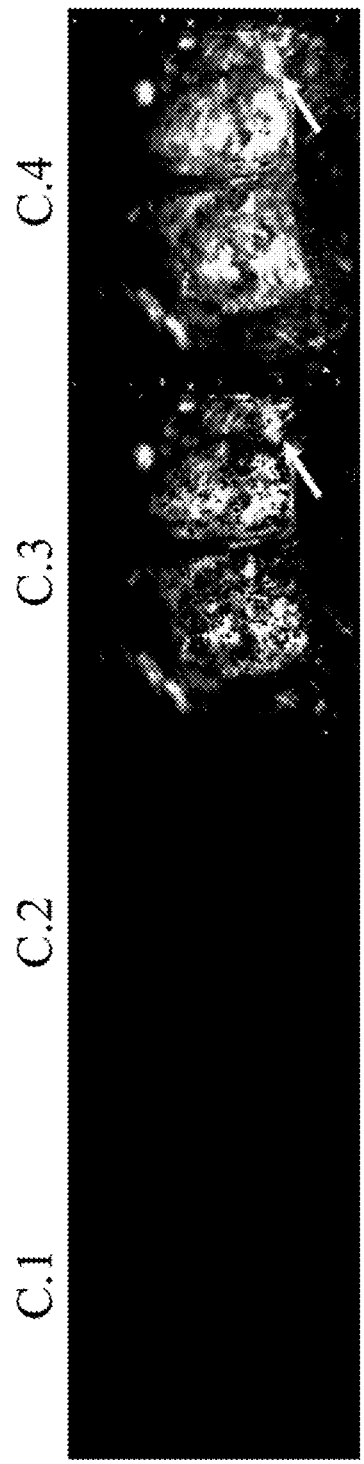

With reference now to FIG. 7C, a series of dynamic parametric images are shown, obtained by applying the solution according to an embodiment of the invention, such images (C.1, C.2, C.3 and C.4) being taken at the same instants as above. Particularly, each pixel has a value that represents the wash-in rate that is calculated for the corresponding location as described above (with the brightness of the pixel in proportion to the local wash-in rate); the pixel remains at a null value (represented in black) until the wash-in rate is calculated i.e., until the detection of the corresponding peak.

Therefore, the images C.1 and C.2 are completely black, since during the wash-in phase no wash-in rate is yet available. However, as shown in the images C.3 and C.4, the suspicious region is now clearly identified against the parenchymal tissue (since they have very different wash-in rates); moreover, this difference is maintained even during the (late) wash-out phase (as shown in the image C.4). Therefore, this enhances the conspicuity of the suspicious region throughout the whole analysis process. At the same time, the high resolution of the images C.3-C.4 also reveals the finest details of the microvascular network of the prostate. This means that the images C.3-C.4 may be used both to detect and to characterize any lesion in the prostate in real-time.

Figure 7D:
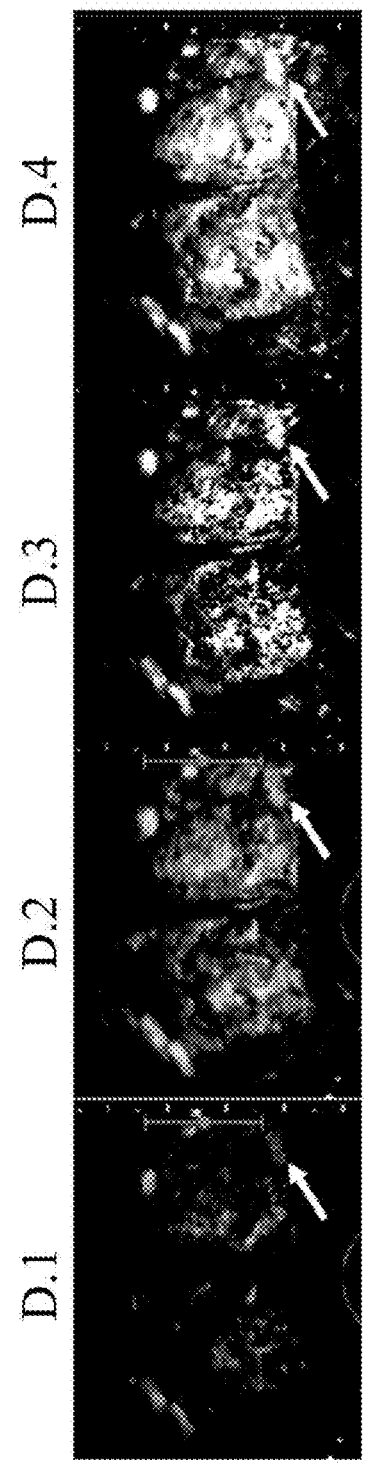

FIG. 7D instead shows a series of overlaid images obtained by overlaying the dynamic parametric images on the corresponding maximum-hold images (denoted with D.1, D.2, D.3 and D.4 in the figure for the same instants). Particularly, each pixel has a value as defined in the corresponding maximum-old image; this value is replaced with the representation of the corresponding wash-in rate as soon as it is calculated (and preferably if it exceeds a predefined threshold value).

Therefore, the images D.1 and D.2 clearly show the early enhancement of the contrast agent and the finest details of the typical microvascular network for the suspicious region during the wash-in phase. During the wash-out phase, the images D.3 and D.4 then provide parametric information of the wash-in rate in the suspicious region at high resolution (thereby maintaining the finest details of its microvascular network). As a result, any lesion of the prostate can be detected in real-time during the wash-in phase, with the corresponding wash-in rates appearing during the wash-out phase, which can subsequently be used for its characterization. Moreover, the final image that is obtained at the end of the analysis process provides an overview or summary of both the perfusion kinetics and the vascular properties of the prostate for improved detection and characterization of any lesion.

Figure 8C:
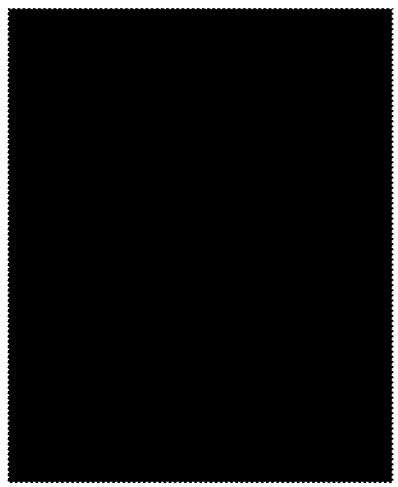
Figure 8C:
Figure 8C:
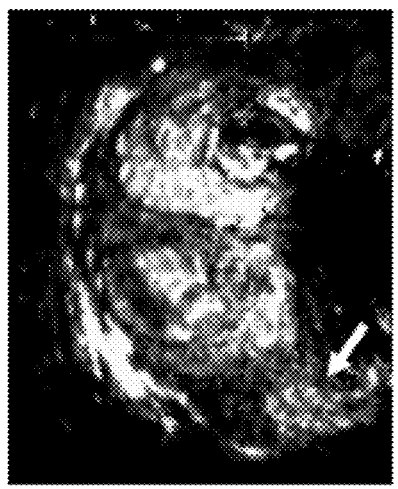

Another example of in-vivo application of the solution according to an embodiment of the invention compared with techniques known in the art is shown in FIG. 8A-FIG. 8C (again for prostate cancer diagnosis). Particularly, FIG. 8A shows a series of original images of the prostate, FIG. 8B shows a series of corresponding maximum-hold images, and FIG. 8C show a series of corresponding dynamic parametric images. The different images of FIG. 8A, FIG. 8B and FIG. 8C are taken at the same instants of the analysis process; more specifically, the first set of images (A.1', B.1' and C.1', respectively) relate to an early wash-in phase, the second set of images (A.2', AB.2' and C.2', respectively) relate to a late wash-in phase, and the third set of images (A.3', B.3' and C.3', respectively) relate to a late wash-out phase.

With reference in particular to FIG. 8A (original images), in this case as well a suspicious region, with an early enhancement of the contrast agent can be seen during the wash-in phase (images A.1' and A.2') in the right peripheral zone of the prostate (as indicated by an arrow on the lower-left side in the images). However, the early enhancement in the suspicious region rapidly disappears during the wash-out phase (image A.3'), so that any information about its location is completely lost.

Moving to FIG. 8B (maximum-hold images), the suspicious region is better defined and delineated during the wash-in phase (images B.1' and B.2'); particularly, the suspicious region now becomes apparent already during the early wash-in phase (image B.1'), whereas in the corresponding original image (A.1' in FIG. 8A) it is hardly visible. However, during the wash-out phase the image B.3' becomes diffuse, and the suspicious region is less conspicuous.

With reference now to FIG. 8C (dynamic parametric images), the images C.1' and C.2' are again completely black during the wash-in phase. Conversely, as shown in the image C.3', the suspicious region is now clearly identified against the parenchymal tissue during the wash-out phase, and it maintains its conspicuity even at a late stage thereof; at the same time, the high resolution of the image C.3' also reveals the finest details of the microvascular network of the suspicious region (which can be used for its improved detection and characterization).

Figure 9A:
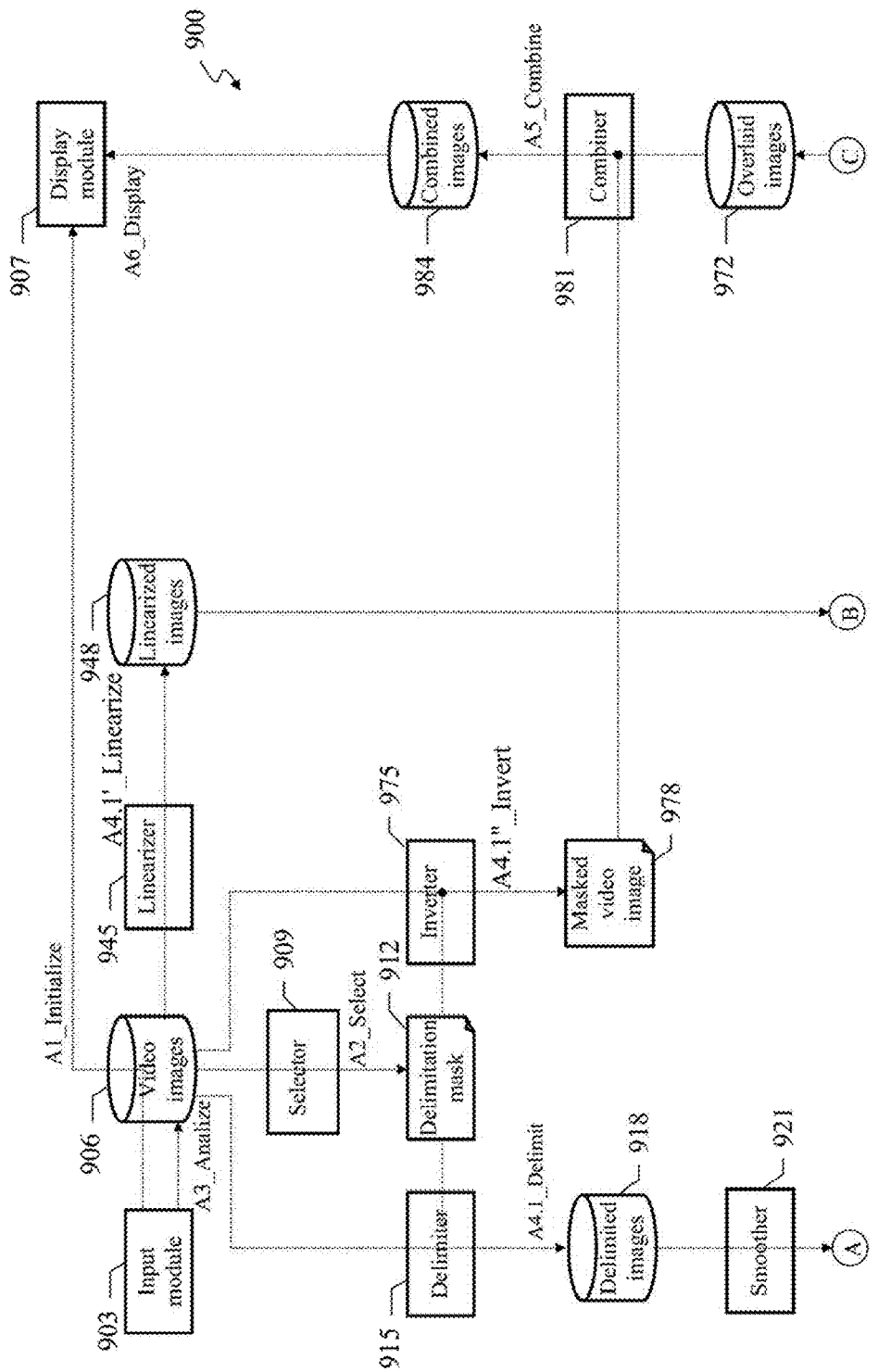
FIG. 9A-9B show a diagram representing the roles of the main components that may be used to implement the solution according to an embodiment of the invention.
Figure 9:
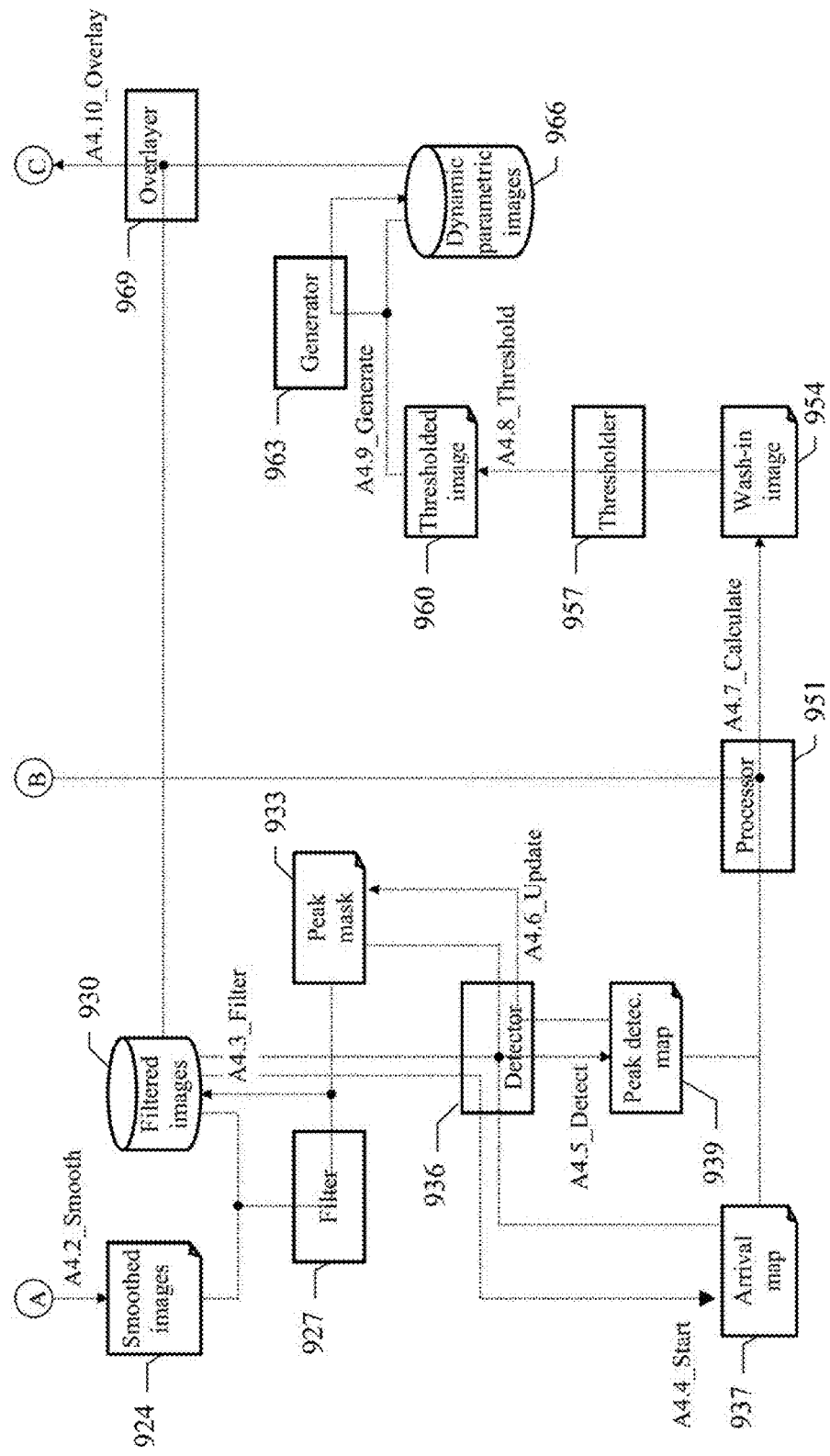

A collaboration diagram representing the main software and/or hardware components that may be used to implement the solution according to an embodiment of the invention is illustrated in FIGS. 9A-9B. These components are denoted as a whole with the reference 900; particularly, the information (programs and data) is typically stored on the hard-disk and loaded (at least partially) into the working memory of a data processing system (for example, the ultrasound scanner or a distinct personal computer) when the programs are running, together with an operating system and other application programs (not shown in the figure). The programs are initially installed onto the hard disk, for example, from DVD-ROM. More specifically, the figure describes the static structure of the system (by means of the corresponding components) and its dynamic behavior (by means of a series of exchanged messages, each one representing a corresponding action, denoted with sequence numbers preceded by the symbol "A").

Particularly, an input module 903 includes a driver that controls the imaging probe. For example, the imaging probe driver is provided with a transmit beam former and pulsers for generating the ultrasound pulses to be applied to the body-part under analysis; the imaging probe then receives the (analog RF) echo signal that is reflected by each location of the body-part in a selected scan plane. The RF analog echo signal is supplied to a receive processor, which pre-amplifies the analog RF echo signal and applies a preliminary time-gain compensation (TGC); the analog RF echo signal is then converted into digital values by an Analog-to-Digital Converter (ADC), and combined into a focused beam signal through a receive beam former. The digital signal so obtained is preferably processed through further digital algorithms and other linear or non-linear signal conditioners (for example, a post-beam-forming TGC). Particularly, the receive processor applies a contrast-specific algorithm to suppress the contribution of the tissue (such as based on the above-mentioned HI, PI, PM or CPS techniques). The digital signal is then demodulated, log-compressed (in order to obtain images with well-balanced contrast), and scan-converted into a video format. This process generates a sequence of (video) images, which are stored into a corresponding repository 906—hereinafter, the different memory structures and their contents will be denoted with the same references for the sake of simplicity.

At the beginning of the analysis process, an operator of the ultrasound scanner actuates the imaging probe and moves it around the body-part to be analyzed (before administering any contrast agent). The corresponding video images 906 are provided in succession to a display module 907 as soon as they are acquired, so as to obtain their display in real-time (action "A1_Initialize"). The operator chooses a scan plane representing the region of the body-part to be analyzed (preferably including a suspicious region) and keeps the imaging probe in a fixed position. A selector 909' is then used by the operator to select a region of interest in the corresponding video image 906 (for example, by drawing a line around it with the help of the trackball). The operation generates a delimitation mask 912 (action "A2_Select"). The delimitation mask 912 consists of a matrix of binary values with the same size as the video images 906; all binary values for the pixels inside the region of interest are assigned the logical value 1, whereas the binary values for the pixels outside the region of interest are assigned the logical value 0.

The contrast agent is then administered to the patient, and the ultrasound scanner acquires a series of further video images 906 representing the perfusion process in the selected scan plane of the body-part (action "A3_Analyze"). A delimiter 915 multiples each current video image 906 by the delimitation mask 912 pixel-by-pixel. This operation generates a corresponding delimited image; the delimited image includes the pixel values of the corresponding video image 906 for the pixels inside the region of interest (as defined by the delimitation mask 912), while the other pixel values are reset to 0. The delimited image is inserted into a repository 918 (action "A4.1_Delimit"). The repository 918 consists of a shift register with a depth equal to the smoothing length m; therefore, for each new delimited image that is inserted into the repository 918, it already includes a number of preceding delimited images equal to m−1 (after an initial transient period).

The repository of the delimited images 918 is accessed by a smoother 921, which applies the smoothing algorithm to each current delimited image (just inserted into the repository 918); this operation generates a corresponding smoothed image 924, which is continually overridden for each new delimited image 918 (action "A4.2_Smooth"). Particularly, the smoothed image 924 is obtained by applying the smoothing function for each pixel of the delimited image 918 having a value different from 0 in the delimitation mask 912 (i.e., inside the region of interest).

A filter 927 applies the filtering algorithm to each new version of the smoothed image 924, so as to generate a corresponding filtered image that is added in succession to a repository 930 (action "A4.3_Filter"). For this purpose, the filter 927 also accesses a peak mask 933 consisting of a matrix of binary values with the same size as the video images 906; for each pixel, the peak mask 933 includes a flag that has the logical value 0 before the detection of the corresponding peak, and it is assigned the logical value 1 afterward (with the flags of all the pixels that are reset to the logical value 0 at the beginning of the analysis process). The filter 927 may apply either the maximum intensity projection algorithm or the minimum intensity projection algorithm according to the content of the peak mask 933. Particularly, for each pixel of the smoothed image 924 having a value different from 0 in the delimitation mask 912 (i.e., inside the region of interest), the filter 927 calculates the maximum (when the corresponding flag in the peak mask 933 has the logical value 0) or the minimum (when the corresponding flag in the peak mask 933 has the logical value 1) between the pixel value in the smoothed image 924 and the pixel value in the preceding filtered image 930.

The repository of filtered images 930 is accessed by a detector 936 (for detecting the instants of interest). Particularly, the detector 936 verifies each current filtered image 930 to detect the arrival of the contrast agent. The detector 936 updates an arrival map 937 accordingly (action "A4.4_Start"). The arrival map 937 consists of a matrix of values with the same size as the video images 906; for each pixel, the value in the arrival map 937 represents the corresponding arrival instant (with the values of all the pixels that are reset to 0 at the beginning of the analysis process). For this purpose, for each pixel of the filtered image 930 having a value different from 0 in the delimitation mask 912 (i.e., inside the region of interest) and whose value in the arrival map 937 is equal to 0 (i.e., the arrival instant has not been detected yet), the detector 936 verifies whether the pixel value in the filtered image 930 exceeds a predefined threshold (indicative of the presence of a significant amount of contrast agent in the corresponding location—for example, 1-5% of a maximum allowable value); if so, the value in the arrival map 937 is set to the image number of the filtered image 930 in the corresponding sequence. In this way, after the detection of the arrival of the contrast agent in the corresponding location, each value of the arrival map 937 will include an arrival number expressing the arrival instant in terms of image number (with the arrival instant equal to the arrival number multiplied by the inverse of the frame rate of the video images 906).

When the repository 930 includes a number of filtered images equal to the stability length L, the detector 936 also starts monitoring the filtered images to detect the peaks of the echo signals. This operation generates a peak detection map 939, which is continually overridden for each new filtered image (action "A4.5_Detect"). The peak detection map 939 consists of a matrix of values with the same size as the video images 906; for each pixel, the value in the peak detection map 939 represents the corresponding peak instant in response to its detection or it is 0 otherwise. For this purpose, for each pixel of the filtered image 930 having a value different from 0 in the delimitation mask 912 (i.e., inside the region of interest), whose value in the arrival map 937 is different from 0 (i.e., the arrival instant has already been detected), and whose flag in the peak mask 933 has the logical value 0 (i.e., the peak has not been detected yet), the detector 936 verifies whether the stability condition is satisfied in the filtered images 930. If so, the value in the peak detection map 939 is set to the image number of the filtered image 930 in the corresponding sequence minus the stability length L−1. In this way, at the detection of the peak of the echo signal in the corresponding location, each value of the peak detection map 939 will include the peak number (expressing the peak instant in terms of image number).

The detector 936 then updates the content of the peak mask 933 accordingly (action "A4.6_Update"). Particularly, for each pixel having the corresponding value in the peak detection map 939 different from 0 (i.e., the peak has just been detected), the detector 936 assigns the logical value 1 to the corresponding flag in the peak mask 933. As a result, the peak mask 933 will accumulate the detection of the peaks in the different filtered images 930 by the detector 936 (so as to prevent their loss due to the override of the peak detection map 939 when new filtered images 930 are processed); therefore, as soon as the peak of each pixel is detected (and the corresponding flag in the peak mask 933 is set to the logical value 1), for this pixel the filter 927 switches to the minimum intensity projection algorithm and the pixel is discarded by the detector 936 when processing new filtered images 930.

At the same time, for each current video image 906 a linearizer 945 generates a corresponding linearized image that is added in succession to a repository 948 (action "A4.1'_Linearize"). Each pixel value of the linearized image 948 is obtained from the corresponding pixel value of the video image 906 by making it directly proportional to the local concentration of the contrast agent; for example, this result can be achieved by applying an inverse log-compression and then squaring the value so obtained (for example, as described in WO-A-2004/110279, the entire disclosures of which is herein incorporated by reference).

A processor 951 accesses the arrival map 937, each new version of the peak detection map 939, and the repository of linearized images 948 (for calculating the wash-in rates). For this purpose, for each pixel having the corresponding value in the peak detection map 939 different from 0 (i.e., the peak has just been detected), the processor 951 retrieves the corresponding pixel value in the linearized image 948 with the number equal to the value in the peak detection map 939 (i.e., the peak number); this pixel value then represents the peak value for said pixel (linearized so as to be directly proportional to the concentration of the contrast agent); the information is used to calculate the corresponding wash-in rate—as the ratio between the peak value (from the linearized images 948) and the wash-in duration. The wash-in duration is obtained as the difference between the value in the peak detection map 939 (i.e., the peak number) and the value in the arrival map 937 (i.e., the arrival number) multiplied by the inverse of the frame rate of the video images 906. This operation generates a wash-in image 954, which is continually overridden for each new filtered image (action "A4.7_Calculate"). For each pixel, the wash-in image 954 includes the corresponding wash-in rate that has been calculated in response to the detection of its peak, or the value 0 otherwise. The processor 951 optionally represents each wash-in rate with a corresponding discrete value (for example, consisting of 64 or 128 levels that are uniformly distributed between the lowest value and the highest value of all the pixels, by possibly applying a gain factor). In this case, the processor 951 also accesses a color lookup table (not shown in the figure), which associates all the possible levels with the representation of corresponding colors (that are preferably brighter as the levels increase); for example, each color is defined by an index for accessing a location within a palette containing its actual specification. The wash-in rate is then replaced with the corresponding color representation before its addition to the wash-in image 954.

A thresholder 957 accesses each new version of the wash-in image 954 (for keeping significant information only). Particularly, the thresholder 957 generates a corresponding thresholded image 960 (action "A4.8_Threshold"). The thresholded image 960 is obtained from the wash-in image 954 by resetting (to the value 0) each pixel value that is lower than a predefined threshold (for example, ranging from 0 to 5% of a maximum allowable pixel value in the wash-in images 954). In this way, it is possible to disregard non-significant wash-in rates (for example, due to a motion artifact). The threshold value may be tuned to optimize the quality of the resulting images; however, it should be noted that the application of this thresholding operation may be avoided by simply setting the threshold value to 0 (so as to obtain a threshold image 960 that is exactly the same as the wash-in image 954).

For each new version of the thresholded image 960, a generator 963 creates a corresponding dynamic parametric image that is added in succession to a repository 966 (action "A4.9_Generate"). The dynamic parametric image 966 accumulates the results obtained from the previous versions of the thresholded image 960 (so as to prevent any loss of information due to its override when new wash-in images 954 are generated); particularly, each pixel of the dynamic parametric image 966 remains at the value 0 until the corresponding wash-in rate is calculated, and then it keeps this value afterwards.

An overlayer 969 overlays each current dynamic parametric image 966 on the corresponding filtered image 930 (taken at the same instant); this operation generates an overlaid image that is added in succession to a repository 972 (action "A4.10 Overlay"). Particularly, an overlay mask is generated from the dynamic parametric image 966; the overlay mask consists of a matrix of binary values with the same size as the dynamic parametric image 966; each binary value of the overlay mask is assigned the logical value 0 if the corresponding pixel value in the dynamic parametric image 966 is strictly higher than 0 (and thus it is strictly higher than the threshold value, as well following the thresholding operation being performed on the corresponding wash-in image 954), or it is assigned the logical value 1 otherwise. At this point, the overlayer 969 generates a masked filtered image by multiplying the filtered image 930 by the overlay mask pixel-by-pixel (so as to keep the pixel values of the filtered image 930 that are not included in the dynamic parametric image 966, while the other pixel values are reset to 0). The overlayer 969 then generates the overlaid image 972 by adding the masked filtered image and the dynamic parametric image 966 pixel-by-pixel. En this way, the pixel value in the filtered images 930 are replaced by the corresponding wash-in rates (for values above the threshold) as soon as they are calculated.

At the same time, an inverter 975 generates an inverted delimitation mask from the delimitation mask 912 (by exchanging its logical values 0 and 1). At this point, the inverter 975 generates a masked video image 978 by multiplying the current video image 906 by the inverted delimitation mask pixel-by-pixel (so at to keep information of the current video image 906 outside the region of interest only).

A combiner 981 overlays each current overlaid image 972 on the corresponding masked video image 978 (taken at the same instant); this operation generates a corresponding combined image, which is added in succession to a repository 984 (action "A5_Combine"). For this purpose, the overlaid image 972 (having pixel values different from 0 only inside the region of interest) is added to the masked video image 978 (having pixel values different from 0 only outside the region of interest) pixel-by-pixel. As a result, the combined image 984 will include the information of the video image 906 outside the region of interest; inside the region of interest, instead, the combined image 984 will include the information of the filtered image 930, said information being replaced by the wash-in rates once they are calculated. The combined images 984 are provided in succession to the display module 907 as soon as they are generated, so as to obtain their display in real-time (action "A6_Display").

A similar structure (not shown in the figure for the sake of simplicity) may also be used to monitor the filtered images for detecting the instant when the echo signals reach their respective half-peak values. Particularly, the detector 936 generates a half-peak detection map, which is continually overridden for each new filtered image 930. The half-peak detection map consists of a matrix of values with the same size as the video images 906; for each pixel, the value in the half-peak detection map represents the corresponding half-peak instant in response to its detection or it is 0 otherwise. As above, this requires a half-peak mask (consisting of a matrix of binary values with the same size as the video images 906); for each pixel, the half-peak mask includes a flag that has the logical value 0 before the detection of the corresponding half-peak, and it is assigned the logical value 1 afterward (with the flags of all the pixels that are reset to the logical value 0 at the beginning of the analysis process). Particularly, for each pixel of the filtered image 930 having a value different from 0 in the delimitation mask 912 (i.e., inside the region of interest), whose flag in the peak mask 933 has the logical value 1 (i.e., the peak has already been detected) and whose flag in the half-peak mask has the logical value 0 (i.e., the half-peak has not been detected yet), the detector 936 verifies whether the pixel value in the filtered image 930 is lower than the corresponding half-peak value (stored by the detector 936 in a corresponding map when the peak is detected). If so, the value in the half-peak detection map is set to the image number of the filtered image 930 in the corresponding sequence. In this way, at the reaching of the half-peak value of the echo signal in the corresponding location, each value of the half-peak detection map will include a half-peak number expressing the half-peak instant in terms of image number (with the half-peak instant equal to the half-peak number multiplied by the inverse of the frame rate of the video images 906).

The detector 936 then updates the content of the half-peak mask accordingly. Particularly, for each pixel having the corresponding value in the half-peak detection map different from 0 (i.e., the half-peak has just been detected), the detector 936 assigns the logical value 1 to the corresponding flag in the half-peak mask. As a result, the half-peak mask will accumulate the detection of the half-peaks in the different filtered images 930 by the detector 936 (so as to prevent their loss due to the override of the half-peak detection map when new filtered images 930 are processed); therefore, as soon as the half-peak of each pixel is detected (and the corresponding flag in the half-peak mask is set to the logical value 1), the pixel is discarded by the detector 936 when processing new filtered images 930.

The processor 951 accesses each new version of the half-peak detection map and the repository of linearized images 948 (for calculating the wash-out rates). For this purpose, for each pixel having the corresponding value in the half-peak detection map different from 0 (i.e., the half-peak has just been detected), the processor 951 retrieves the corresponding pixel value in the linearized image 948 with the number equal to the value in the half-peak detection map 939 (i.e., the half-peak number); this pixel value then represents the (linearized) half-peak value for said pixel; the information is used to calculate the corresponding wash-out rate—as the ratio between the half-peak value (from the linearized images 948) and the wash-out duration. The wash-out duration is obtained as the difference between the peak number (stored by the detector 936 in a corresponding map when the peak is detected) and the value in the half-peak detection map (i.e., the half-peak number) multiplied by the inverse of the frame rate of the video images 906. This operation generates a wash-out image, which is continually overridden for each new filtered image. For each pixel, the wash-out image includes the corresponding wash-out rate that has been calculated in response to the detection of its half-peak, or the value 0 otherwise. The wash-out images are then processed in a way similar to the wash-in images as described above.

Modifications

Naturally, in order to satisfy local and specific requirements, a person skilled in the art may apply to the solution described above many logical and/or physical modifications and alterations. More specifically, although this solution has been described with a certain degree of particularity with reference to preferred embodiment(s) thereof, it should be understood that various omissions, substitutions and changes in the form and details as well as other embodiments are possible. Particularly, the same solution may even be practiced without the specific details (such as the numerical examples) set forth in the preceding description to provide a more thorough understanding thereof; conversely, well-known features may have been omitted or simplified in order not to obscure the description with unnecessary particulars. Moreover, it is expressly intended that specific elements and/or method steps described in connection with any embodiment of the disclosed solution may be incorporated in any other embodiment as a matter of general design choice.

Particularly, similar considerations apply if the ultrasound scanner has a different structure or includes other units (for example, with an imaging probe of the linear-, convex-, phased-, or matrix-array type). Alternatively, the proposed solution is applied in a medical imaging system that consists of an ultrasound scanner and a distinct computer (or any equivalent data processing system); in this case, the recorded information is transferred from the ultrasound scanner to the computer for its processing (for example, through a digital, analogue or network connection). In any case, the application to any other medical imaging system— for example, based on Magnetic Resonance Imaging (MRI) or X-ray Computed Tomography (CT)—is within the scope of the proposed solution. Moreover, even though in the preceding description reference has been made to prostate cancer diagnosis, this is not to be intended in a limitative manner—with the same solution that may likewise find application in the diagnosis of other types of cancer (for example, in liver and breast), or more generally to arbitrary medical tests.

The proposed solution lends itself to be put into practice with equivalent contrast agents; for example, the contrast agent may be specific for enhancing Magnetic Resonance imaging or X-ray Computed Tomography imaging. Alternatively, the contrast agent may be injected in an intra-arterial, intralymphatic, subcutaneous, intramuscular, intradermal, intraperitoneal, interstitial, intrathecal or intratumoral way, as a continuous infusion (with or without the application of destructive flashes), orally (for example, for imaging the gastro-intestinal tract), via a nebulizer into the airways, and the like. Similar considerations apply if the video images are acquired in any other way (for example, by applying a motion compensation algorithm). Moreover, nothing prevents applying the proposed solution to 3-D video images, to the whole video images (without selecting any region of interest), and the like.

Alternatively, the peak may be detected with different monitoring operations, or more generally with any operation aimed at recording, collecting, verifying and/or comparing the progress of the filtered signal over time (including variations or steadiness thereof); for example, this operation may be implemented with continuous or discontinuous verifications of the stability condition, said verification being performed either at regular or variable time intervals (i.e., at monitoring instants that are not necessarily the same as the acquisition instants of the video images). In any case, although the proposed technique has been specifically designed for use in real-time, the examination of the obtained results off-line is within the scope of the solution according to an embodiment of the invention (for example, after transferring the recorded information from the ultrasound scanner to the computer through a removable disk or a memory key).

Moreover, the stability length may be set to different values, or it may be determined dynamically (for example, according to an estimated flow rate of the contrast agent). In any case, the use of alternative stability conditions is not excluded; for example, when the filtering operation is based on a mean function, it is possible to detect the peak when the variations of the filtered signal remain within a predefined range in the stability window.

As already pointed out, the information relating to the detection of the peaks may be used for a number of purposes. For example, in a different embodiment of the proposed solution only the filtered images are generated (without the calculation of any perfusion parameter); the filtered images are then displayed (possibly overlaid on the video images) so as to provide an enhanced visual perception of the perfusion process. Particularly, the application of the maximum intensity projection algorithm before the peak instants facilitates the detection and characterization of any suspicious region (since their early enhancement of the contrast agent is better defined and delineated at full-resolution). At the same time, the application of the minimum intensity projection algorithm after the peak instants provides useful information relating to the wash-out phase; this allows preserving the conspicuous representation of the suspicious region during the whole analysis process.

The video images may be linearized in a different way; for example, the linearized images might be already available for other purposes (such as when parametric analyses are implemented); in this case, it is possible to exploit the available information without any additional linearization operation. Anyway, the application of the filtering algorithm directly on the linearized images or the use of the video images alone is not excluded.

The application of the filtering function to the video images is not to be interpreted in a limitative manner; indeed, nothing prevents filtering the raw echo signals directly in a similar way (even in the analog domain).

The implementation described above assumes a direct relation between the intensity of the echo signal and each corresponding pixel value (i.e., a larger intensity of the echo signal results in a brighter pixel); conversely, in a system based on negative images (wherein the pixel values decrease with the intensity of the echo signals) all the equations given above would need to be modified to reflect the reverse logic. Of course, when only the wash-in rates have to be calculated, it is possible to apply the maximum intensity projection algorithm alone (up to the detection of the peaks).

Alternatively, similar filtering functions may be used (even of the same type throughout the whole analysis process); for example, it is possible to calculate each pixel value in the filtered images as the average of the corresponding pixel values in a set of video images; these video images include the one taken at the current instant, in addition to one or more other video images taken at preceding and/or following instants.

The smoothing length may be set to different values, or it may be determined dynamically (for example, according to an estimated quality of the video images). In any case, the use of equivalent smoothing functions is feasible (for example, the mean function). However, the application of the smoothing algorithm to the video images (before the application of the filtering algorithm) is not strictly necessary, and it may be omitted in specific scenarios (for example, when the quality of the video images is relatively high).

The calculated perfusion parameters may be displayed in a different way; for example, nothing prevents generating a single (static) parametric image for each perfusion parameter as soon as it has been calculated for all the pixels of interest.

The threshold value may be set to different values, or it may be determined dynamically (for example, according to an estimated maximum value of the wash-in rates). In any case, this feature is not strictly necessary, and it may be omitted in a simplified implementation of the proposed solution (wherein all the wash-in rates are included in the dynamic parametric images irrespectively of their values— so as to leave the assessment of the corresponding significance to the operator).

The choice of how to display the obtained results may also be left to the preference of the operator. For example, it is possible to display the overlaid images alone (i.e., without combining them with the masked video images), the dynamic parametric images alone (i.e., without combining them with the filtered images), the dynamic parametric images combined with the masked video images (in order to display the perfusion parameters against a black background in the region of interest for improved contrast), and the like. Alternatively, the filtered images may be combined with (original) non contrast-specific images—such as fundamental B-mode images being obtained from the echo signals directly.

Naturally, the monitoring of the filtered signals may be limited to the detection of the instants required to calculate the desired perfusion parameters (for example, only the arrival instant in addition to the peak instant for the wash-in rate). Moreover, the calculation of the wash-out rate may be based on the detection of another instant when the filtered signal reaches a different percentage of the peak value (for example, 40-60% of its value).

In different applications of the proposed solution, it is possible to calculate only some of the proposed perfusion parameters—down to a single one of them (i.e., only the wash-in rate, the wash-out rate or the product of the wash-in and wash-out rates). More generally, nothing prevents calculating any other additional and/or alternative perfusion parameters (for example, a blood volume, a mean velocity, a maximum intensity, a time-to-peak, a wash-in time, a time-of-arrival, a square-root of the peak value divided by the square of the wash-in duration, and the like).

The application of the proposed solution to multiple regions of the body-part with a single bolus injection of the contrast agent may be implemented in different ways (for example, by applying the flash only after the detection of the half-peaks). In any case, this feature is merely optional (with a single examination that is normally performed during the whole analysis process).

The proposed solution lends itself to be put into practice with an equivalent method (by using similar steps, removing some steps being non-essential, or adding further optional steps); moreover, the steps may be performed in a different order, concurrently or in an interleaved way (at least in part).

This solution may be implemented as a plug-in for a pre-existing control program of the ultrasound scanner, directly in the same control program, or as a stand-alone application (even running on a distinct computer or provided as a network service). Similar considerations apply if the program (which may be used to implement each embodiment of the invention) is structured, in a different way, or if additional modules or functions are provided; likewise, the memory structures may be of other types, or may be replaced with equivalent entities (not necessarily consisting of physical storage media). In any case, the program may take any form suitable to be used by any data processing system or in connection therewith (for example, within a virtual machine); particularly, the program may be in the form of external or resident software, firmware, or microcode (either in object code or in source code—for example, to be compiled or interpreted). Moreover, it is possible to provide the program on any computer-usable medium; the medium can be any element suitable to contain, store, communicate, propagate, or transfer the program. For example, the medium may be of the electronic, magnetic, optical, electromagnetic, infrared, or semiconductor type; examples of such medium are fixed disks (where the program can be pre-loaded), removable disks, tapes, cards, wires, fibers, wireless connections, networks, broadcast waves, and the like. In any case, the solution according to an embodiment of the present invention lends itself to be implemented even with a hardware structure (for example, integrated in a chip of semiconductor material), or with a combination of software and hardware.

The above-described solution, as well as any modification thereof, can advantageously be used in a conventional diagnostic method. The diagnostic method typically includes administering the contrast agent to the body-part, and acquiring input signals from the body-part for the execution of the proposed operations. As mentioned above, the administration of the contrast agent is typically performed intravenously, preferably as a bolus injection. Moreover, the acquisition of the input signals may be performed by insonating the body part (by means of an ultrasound scanner generating a pulsed ultrasound wave with a predetermined center transmit frequency), receiving the echo signals originating from the body part, and processing them in a way to generate images representative of the same body part. The diagnostic method may also include the further step of applying at least one destruction pulse to the body-part to cause a substantial destruction of the contrast agent therein. In general, each step of applying the destruction pulse is followed by a further respective series of steps of insonating the body-part, receiving the corresponding echo signals and processing them as mentioned above.

The invention claimed is:

1. A process for generating diagnostic data from an imaging procedure, the process comprising:
    administering a contrast agent to a body-part;
    applying an interrogating stimulus to the body-part being perfused with the contrast agent;
    recording, into a memory of a data processing system, an input signal acquired in response to the interrogating stimulus that is applied to the body part being perfused with a contrast agent;
    generating and storing into the memory of the data processing system a filtered signal from the input signal, the filtered signal being generated by:
        comparing the intensity of a comparison signal, equal to the input signal or to a smoothed signal obtained by applying a smoothing function to the input signal and at least one previous input signal provided during the imaging procedure, with the intensity of a previous filtered signal generated from a previous input signal provided during the imaging procedure, the previous filtered signal being set to a previous comparison signal provided during the imaging procedure at a first iteration, and then
        if the intensity of the comparison signal is representative of a response to the interrogating stimulus that is greater than the response of the previous filtered signal, then the intensity of the filtered signal equals the intensity of the comparison signal, otherwise the intensity of the filtered signal equals the intensity of the previous filtered signal;
    after a predetermined number of filtered signals have been generated, monitoring the filtered signal by the data processing system to determine whether a stability condition has been fulfilled, the stability condition being fulfilled when the intensity of the filtered signal remains within a predefined range of variation relative to the intensity of a predefined number of immediately preceding filtered signals;
    repeating the recording, generating and monitoring acts over time until the stability condition is fulfilled, and when fulfilled, establishing a peak in the corresponding filtered signal,
    generating and storing into the memory of the data processing system the diagnostic data according to the filtered signals and the detection of the peak; and displaying at least a representation of the diagnostic data according to the deletion of the peak, on a monitor of the data processing system for evaluating the body-part.

2. The process according to claim 1, wherein said monitoring the filtered signal includes:
stopping the monitoring after the stability condition has been fulfilled.

3. The process according to claim 2, wherein:
said establishing a peak includes setting the peak to an instant preceding the instant at which the stability condition is fulfilled by a stability time-window corresponding to said predefined number of immediately preceding filtered signals.

4. The process according to claim 1, further comprising calculating at least one perfusion parameter indicative of a perfusion of the location of the body-part according to the peak.

5. The process according to claim 4, wherein said calculating at least one perfusion parameter includes:
generating a linearized input signal from the input signal, the linearized input signal being proportional to a concentration of the contrast agent in the corresponding location of the body-part, and
calculating said at least one perfusion parameter according to the linearized input signal at one or more instants being determined by said monitoring.

6. The process according to claim 4, wherein said monitoring the filtered signal includes detecting an arrival instant at which the filtered signal exceeds a threshold value and establishing a peak instant indicative of an instant of detection of the peak, and calculating at least one perfusion parameter includes determining a peak value indicative of a response to the interrogating stimulus at the peak instant.

7. The process according to claim 6, wherein said calculating at least one perfusion parameter includes:
calculating a wash-in rate according to a ratio between the peak value and a difference between the peak instant and the arrival instant.

8. The process according to claim 6, wherein said monitoring the filtered signal includes:
detecting an arrival instant at which the filtered signal exceeds a threshold value and detecting a peak instant indicative of an instant of detection of the peak, and calculating at least one perfusion parameter includes determining a peak value indicative of a response to the interrogating stimulus of the corresponding selected location at the peak instant, and
detecting a reduction instant indicative of an instant of reaching of a reduction value by the filtered signal, the reduction value being a predefined percentage of the peak value.

9. The process according to claim 8, wherein said calculating at least one perfusion parameter includes:
calculating a wash-in rate according to a ratio between the peak value and a difference between the peak instant and the arrival instant,
calculating a wash-out rate according to a ratio between the reduction value and a difference between the reduction instant and the peak instant, and
calculating a product between the wash-in rate and the wash-out rate.

10. The process according to claim 1, wherein:
said recording an input signal includes recording a sequence of input images each one including a plurality of input signals each one indicative of the response to the interrogating stimulus of a corresponding location of the body-part,
said generating a filtered signal includes generating a sequence of filtered images from the input images, for each selected location each filtered image including the filtered signal being generated from the corresponding input signal.

11. The process according to claim 10, wherein said generating a sequence of filtered images includes, after said establishing the peak:
comparing the intensity of the comparison signal with the intensity of the previous filtered signal and then if the intensity of the comparison signal is representative of the response lower than the response of the previous filtered signal, then the intensity of the filtered signal equals the intensity of the comparison signal, otherwise the intensity of the filtered signal equals the intensity of the previous filtered signal.

12. The process according to claim 10, further comprising:
calculating at least one perfusion parameter indicative of a perfusion of the location of the body-part according to the peak, and
generating at least one sequence of dynamic parametric images, in each of said at least one sequence of dynamic parameter images for each location each dynamic parametric image including a null value before said calculating a corresponding one of said at least one perfusion parameter and a value indicative of the corresponding perfusion parameter after said calculating the corresponding perfusion parameter.

13. The process according to claim 12, wherein said generating at least one sequence of dynamic parametric images includes maintaining the null value for each location of each dynamic parametric image after said calculating the corresponding perfusion parameter when the corresponding perfusion parameter does not reach a threshold value.

14. The process according to claim 12, further comprising generating a sequence of overlaid images for each sequence of dynamic parametric images, the overlaid images being generated by overlaying each dynamic parametric image on a corresponding filtered image.

15. The process according to claim 1, further comprising:
applying a destruction pulse to the body-part to cause a destruction of the contrast agent for at least 50% of a local concentration thereof before said applying the destruction pulse;
repeating, at least once:
said recording an input signal,
said generating a filtered signal,
said monitoring the filtered signal, and
said establishing a peak,
after said applying the destruction pulse.

16. A diagnostic method comprising:
administering a contrast agent to a body-part;
applying an interrogating stimulus to a location of the body-part being perfused with the contrast agent;
acquiring a plurality of input signals over a plurality of instants in time, each input signal indicative of a response to a corresponding interrogating stimulus at one of the instants in time, the plurality of input signals being processed by the process according to claim 1 thereby displaying said representation of the diagnostic data; and
evaluating the body-part according to the representation of the diagnostic data.

17. A computer program product including a non-transitory computer-readable medium storing a computer program, the computer program being loadable into a working memory of a data processing system thereby configuring the data processing system to perform a process for generating diagnostic data from an imaging procedure when the computer program is executed on the data processing system, the process comprising:
recording, into a memory of a data processing system, an input signal acquired in response to an interrogating stimulus that is applied to a location of a body part being perfused with a contrast agent;
generating and storing into the memory of the data processing system a filtered signal from the input signal, the filtered signal being generated by:
comparing the intensity of a comparison signal, equal to the input signal or to a smoothed signal obtained by applying a smoothing function to the input signal and at least one previous input signal provided during the imaging procedure, with the intensity of a previous filtered signal generated from a previous input signal provided during the imaging procedure, the previous filtered signal being set to a previous comparison signal provided during the imaging procedure at a first iteration, and then
if the intensity of the comparison signal is representative of a response to the interrogating stimulus that is greater than the response of the previous filtered signal, then the intensity of the filtered signal equals the intensity of the comparison signal, otherwise the intensity of the filtered signal equals the intensity of the previous filtered signal;
after a predetermined number of filtered signals have been generated, monitoring the filtered signal by the data processing system to determine whether a stability condition has been fulfilled, the stability condition being fulfilled when the intensity of the filtered signal remains with a predefined range of variation relative to the intensity of a predefined number of immediately preceding filtered signals;
repeating the recording, generating and monitoring acts over time until the stability condition is fulfilled, and when fulfilled, establishing a peak in the corresponding filtered signal;
generating and storing into the memory of the data processing system the diagnostic data according to the filtered signals and to the detection of the peak; and
displaying at least a representation of the diagnostic data according to the detection of the peak, on a monitor of the data processing system for evaluating the body-part.

18. A diagnostic system for generating diagnostic data from an imaging procedure, the system comprising:
a circuit for applying an interrogating stimulus to a body-part perfused with a contrast agent;
a circuit for recording, into a memory of a data processing system, an input signal acquired in response to the interrogating stimulus that is applied to the body part;
a circuit for generating and storing into the memory of the data processing system a filtered signal from the input signal, the filtered signal being generated by:
comparing the intensity of a comparison signal, equal to the input signal or to a smoothed signal obtained by applying a smoothing function to the input signal and at least one previous input signal provided during the imaging procedure, with the intensity of a previous filtered signal generated from a previous input signal provided during the imaging procedure, the previous filtered signal being set to a previous comparison signal provided during the imaging procedure at a first iteration, and then
if the intensity of the comparison signal is representative of a response to the interrogating stimulus that is greater than the response of the previous filtered signal, then the intensity of the filtered signal equals the intensity of the comparison signal, otherwise the intensity of the filtered signal equals the intensity of the previous filtered signal;
a circuit of the data processing system for monitoring the filtered signal to determine whether a stability condition has been fulfilled after a predetermined number of filtered signals have been generated, the stability condition being fulfilled when the intensity of the filtered signal remains within a predefined range of variation relative to the intensity of a predefined number of immediately preceding filtered signals;
a circuit for causing the other circuits to repeat their respective recording, generating and monitoring acts over time until the stability condition is fulfilled, and when fulfilled, establishing a peak in the corresponding filtered signal;
a circuit for generating and storing into the memory of the data processing system diagnostic data according to the filtered signals and the detection of the peak; and
a circuit for displaying at least a representation of the diagnostic data according to the detection of the peak, on a monitor of the data processing system for evaluating the body-part.

19. The diagnostic system according to claim 18, wherein the circuit for monitoring the filtered signal includes:
a circuit for stopping the monitoring after the stability condition has been fulfilled.

20. The diagnostic system according to claim 19, wherein:
the circuit for establishing the peak includes a circuit for setting the peak to an instant preceding the instant at which the stability condition is fulfilled by a stability time-window corresponding to said predefined number of immediately preceding filtered signals.

21. The diagnostic system according to claim 18, further comprising a circuit for calculating at least one perfusion parameter indicative of a perfusion of the location of the body-part according to the peak.

22. The diagnostic system according to claim 21, wherein the circuit for calculating at least one perfusion parameter includes:
a circuit for generating a linearized input signal from the input signal, the linearized input signal being proportional to a concentration of the contrast agent in the location of the body-part, and
a circuit for calculating said at least one perfusion parameter according to the linearized input signal at one or more instants being determined by the circuit for monitoring.

23. The diagnostic system according to claim 21, wherein the circuit for monitoring the filtered signal includes a circuit for detecting an arrival instant at which the filtered signal exceeds a threshold value and a circuit for establishing a peak instant indicative of an instant of detection of the peak, and the circuit for calculating at least one perfusion parameter includes a circuit for determining a peak value indicative of a response to the interrogating stimulus at the peak instant.

24. The diagnostic system according to claim 23, wherein the circuit for calculating at least one perfusion parameter includes:
- a circuit for calculating a wash-in rate according to a ratio between the peak value and a difference between the peak instant and the arrival instant.

25. The diagnostic system according to claim 21, wherein the circuit for monitoring the filtered signal includes:
- a circuit for detecting an arrival instant at which the filtered signal exceeds a threshold value and a circuit for detecting a peak instant indicative of an instant of detection of the peak, and the circuit for calculating at least one perfusion parameter includes a circuit for determining a peak value indicative of a response to the interrogating stimulus of the corresponding selected location at the peak instant, and
- a circuit for detecting a reduction instant indicative of an instant of reaching of a reduction value by the filtered signal, the reduction value being a predefined percentage of the peak value.

26. The diagnostic system according to claim 25, wherein the circuit for calculating at least one perfusion parameter includes:
- a circuit for calculating a wash-in rate according to a ratio between the peak value and a difference between the peak instant and the arrival instant,
- a circuit for calculating a wash-out rate according to a ratio between the reduction value and a difference between the reduction instant and the peak instant, and
- a circuit for calculating a product between the wash-in rate and the wash-out rate.

27. The diagnostic system according to claim 18, wherein:
the circuit for recording an input signal includes a circuit for recording a sequence of input images each one including a plurality of input signals each one indicative of the response to the interrogating stimulus of a corresponding location of the body-part,
the circuit for generating a filtered signal includes a circuit for generating a sequence of filtered images from the input images, for each selected location each filtered image including the filtered signal being generated from the corresponding input signal.

28. The diagnostic system according to claim 27, wherein the circuit for generating a sequence of filtered images includes a circuit for, after said detecting the corresponding peak, comparing the intensity of the comparison signal with the intensity of the previous filtered signal and then if the intensity of the comparison signal is representative of the response lower than the response of the previous filtered signal, then the intensity of the filtered signal equals the intensity of the comparison signal, otherwise the intensity of the filtered signal equals the intensity of the previous filtered signal.

29. The diagnostic system according to claim 27, further comprising a circuit for calculating at least one perfusion parameter indicative of a perfusion of a location of the body-part according to the peak, and a circuit for generating at least one sequence of dynamic parametric images, in each of said at least one sequence of dynamic parameter images for each location each dynamic parametric image including a null value before said calculating a corresponding one of said at least one perfusion parameter and a value indicative of the corresponding perfusion parameter after said calculating the corresponding perfusion parameter.

30. The diagnostic system according to claim 29, wherein the circuit for generating at least one sequence of dynamic parametric images includes a circuit for maintaining the null value for each location of each dynamic parametric image after said calculating the corresponding perfusion parameter when the corresponding perfusion parameter does not reach a threshold value.

31. The diagnostic system according to claim 29, further comprising a circuit for generating a sequence of overlaid images for each sequence of dynamic parametric images, the overlaid images being generated by overlaying each dynamic parametric image on a corresponding filtered image.

32. The diagnostic system according to claim 18, further comprising:
- a circuit for applying a destruction pulse to the body-part to cause a destruction of the contrast agent for at least 50% of a local concentration thereof before said applying the destruction pulse, and
- a circuit for repeating at least once an actuation of the circuit recording an input signal, the circuit for generating a filtered signal, the circuit for monitoring the filtered signal and the circuit for establishing a peak.

* * * * *

UNITED STATES PATENT AND TRADEMARK OFFICE
CERTIFICATE OF CORRECTION

PATENT NO. : 10,278,612 B2
APPLICATION NO. : 13/127389
DATED : May 7, 2019
INVENTOR(S) : Peter Frinking et al.

It is certified that error appears in the above-identified patent and that said Letters Patent is hereby corrected as shown below:

In the Claims

Column 27, Line 2, "deletion" should read --detection--.

Column 29, Line 38, "with" should read --within--.

Column 32, Line 41, "circuit recording" should read --circuit for recording--.

Signed and Sealed this
Second Day of July, 2019

Andrei Iancu
*Director of the United States Patent and Trademark Office*